US011446316B2

(12) United States Patent
Davis et al.

(10) Patent No.: US 11,446,316 B2
(45) Date of Patent: Sep. 20, 2022

(54) GALACTOOLIGOSACCHARIDES FOR PREVENTING INJURY AND/OR PROMOTING HEALING OF THE GASTROINTESTINAL TRACT

(75) Inventors: Steven R. Davis, Columbus, OH (US); Jomay Chow, Westerville, OH (US)

(73) Assignee: ABBOTT LABORATORIES, Abbott Park, IL (US)

( * ) Notice: Subject to any disclaimer, the term of this patent is extended or adjusted under 35 U.S.C. 154(b) by 205 days.

(21) Appl. No.: 14/234,166

(22) PCT Filed: Jul. 19, 2012

(86) PCT No.: PCT/US2012/047307
§ 371 (c)(1),
(2), (4) Date: May 6, 2014

(87) PCT Pub. No.: WO2013/016111
PCT Pub. Date: Jan. 31, 2013

(65) Prior Publication Data
US 2014/0294789 A1 Oct. 2, 2014

Related U.S. Application Data

(60) Provisional application No. 61/510,632, filed on Jul. 22, 2011.

(51) Int. Cl.
*A61K 31/702* (2006.01)
*A61K 35/74* (2015.01)
*A61K 45/06* (2006.01)
*A23L 33/00* (2016.01)
*A61K 35/741* (2015.01)
*A61K 35/745* (2015.01)
*A61K 35/747* (2015.01)

(52) U.S. Cl.
CPC ............ *A61K 31/702* (2013.01); *A23L 33/40* (2016.08); *A61K 35/741* (2013.01); *A61K 35/745* (2013.01); *A61K 35/747* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,762,822 A | 8/1988 | Ettinger | |
| 5,013,569 A | 5/1991 | Rubin | |
| 5,260,280 A | 11/1993 | Isoda et al. | |
| 5,834,423 A | 11/1998 | Koketsu et al. | |
| 5,906,982 A | 5/1999 | Prieto et al. | |
| 6,036,992 A | 3/2000 | Borror et al. | |
| 6,045,854 A * | 4/2000 | Prieto | A23L 29/30 426/658 |
| 6,080,787 A | 6/2000 | Carlson et al. | |
| 6,083,934 A | 7/2000 | Prieto et al. | |
| 6,146,670 A | 11/2000 | Prieto et al. | |
| 6,294,206 B1 | 9/2001 | Barrett-Reis | |
| 6,306,908 B1 | 10/2001 | Carlson et al. | |
| 6,365,218 B1 | 4/2002 | Borschel et al. | |
| 6,497,908 B1 | 12/2002 | Oshiro | |
| 6,576,251 B1 | 6/2003 | Stahl et al. | |
| 6,630,452 B2 | 10/2003 | Wilson | |
| 7,090,862 B2 | 8/2006 | Barrett-Reis et al. | |
| 7,090,879 B2 | 8/2006 | Albrecht et al. | |
| 7,101,565 B2 | 9/2006 | Monte | |
| 7,416,752 B2 | 8/2008 | Holub et al. | |
| 8,425,930 B2 * | 4/2013 | Barboza | A61K 31/702 424/439 |
| 8,703,737 B2 | 4/2014 | Buck et al. | |
| 8,771,674 B2 | 7/2014 | Sprenger | |
| 8,802,650 B2 | 8/2014 | Buck et al. | |
| 8,815,312 B2 * | 8/2014 | Falk | A61K 31/353 424/725 |
| 8,926,952 B2 | 1/2015 | Trejo et al. | |
| 9,217,133 B2 | 12/2015 | Sprenger | |
| 9,539,269 B2 | 1/2017 | Chow et al. | |
| 9,795,623 B2 | 10/2017 | Davis et al. | |
| 2002/0019991 A1 | 2/2002 | Prieto et al. | |
| 2003/0060445 A1 | 3/2003 | Wilson | |
| 2004/0001817 A1 | 1/2004 | Giampapa | |
| 2004/0202765 A1 | 10/2004 | McMahon et al. | |
| 2004/0265462 A1 | 12/2004 | Carlson | |
| 2005/0004070 A1 | 1/2005 | Stahl et al. | |

(Continued)

FOREIGN PATENT DOCUMENTS

| | | |
|---|---|---|
| CA | 2655665 | 12/2007 |
| CA | 2724766 | 3/2010 |

(Continued)

OTHER PUBLICATIONS

Nittynen (Galacto-oligosaccharides and bowel function, 2007) (Year: 2007).*
Van Dokkum (Effect of nondigestible oligosaccharides on large-bowel functions, blood lipid concentrations and glucose absorption in young healthy male subjects, 1999). (Year: 1999).*
Deguchi, Yoriko et al. Effects of β 1-4 Galacto-oligosaccharides Administration on Defecation of Healthy Volunteers with Constipation Tendency. vol. 55 No. 1, pp. 13-22. (Year: 1997).*
Amendment for U.S. Appl. No. 13/334,933 dated Jun. 23, 2015.
Final Office Action in U.S. Appl. No. 13/335,341 dated May 4, 2015.
First Office Action in CN 201280051863.0 dated Mar. 27, 2015 (received Apr. 30, 2015).
Search Report and Written Opinion in SG 2013050067 dated May 28, 2015.

(Continued)

*Primary Examiner* — Nghi V Nguyen
(74) *Attorney, Agent, or Firm* — Calfee, Halter & Griswold LLP

(57) ABSTRACT

Disclosed are nutritional compositions including galactooligosaccharides that can be administered to individuals including preterm infants, infants, toddlers, children, and adults for preventing injury and/or improving the healing of the gastrointestinal tract. Additional suitable methods of using the nutritional compositions including the galactooligosaccharides are also disclosed.

8 Claims, 6 Drawing Sheets

(56) References Cited

U.S. PATENT DOCUMENTS

| | | |
|---|---|---|
| 2005/0070464 A1 | 3/2005 | Stahl et al. |
| 2005/0096295 A1 | 5/2005 | McMahon et al. |
| 2005/0208179 A1 | 9/2005 | Albrecht et al. |
| 2006/0039954 A1 | 2/2006 | Gierhart et al. |
| 2006/0088574 A1 | 4/2006 | Manning et al. |
| 2006/0246146 A1 | 11/2006 | McMahon et al. |
| 2006/0247153 A1 | 11/2006 | McMahon et al. |
| 2006/0270739 A1 | 11/2006 | Johnson et al. |
| 2007/0048405 A1 | 3/2007 | DeWille et al. |
| 2007/0058523 A1 | 5/2007 | Willemsen et al. |
| 2007/0098849 A1 | 5/2007 | Barrett-Reis et al. |
| 2007/0104700 A1* | 5/2007 | Garcia-Rodenas ..... A23L 33/21 424/93.45 |
| 2007/0104843 A1 | 5/2007 | Holst et al. |
| 2007/0173480 A1 | 7/2007 | Clandinin et al. |
| 2007/0255598 A1 | 11/2007 | McCarthy |
| 2008/0003329 A1 | 1/2008 | Rueda et al. |
| 2008/0003330 A1 | 1/2008 | Rueda et al. |
| 2008/0015166 A1 | 1/2008 | van Tol et al. |
| 2008/0057178 A1 | 3/2008 | Rueda et al. |
| 2008/0064635 A1 | 3/2008 | Rueda et al. |
| 2008/0089981 A1 | 4/2008 | Butler et al. |
| 2008/0125346 A1 | 5/2008 | Beermann et al. |
| 2009/0082249 A1 | 3/2009 | Garssen et al. |
| 2009/0092590 A1 | 4/2009 | Rangavajila et al. |
| 2009/0098240 A1 | 4/2009 | Mills et al. |
| 2009/0118229 A1 | 5/2009 | Jouni |
| 2009/0143301 A1 | 6/2009 | Olson et al. |
| 2009/0148545 A1* | 6/2009 | Falk ................. A23L 1/202 424/757 |
| 2009/0191151 A1 | 7/2009 | Gai et al. |
| 2009/0305996 A1 | 12/2009 | Beermann et al. |
| 2010/0047393 A1 | 2/2010 | Glas et al. |
| 2010/0063002 A1 | 3/2010 | Stahl et al. |
| 2010/0233129 A1 | 9/2010 | Fichot et al. |
| 2010/0233198 A1 | 9/2010 | Fichot et al. |
| 2010/0254949 A1* | 10/2010 | Barboza ............... A61K 31/702 424/93.4 |
| 2010/0260720 A1 | 10/2010 | Sprenger |
| 2010/0298244 A1 | 11/2010 | Yang et al. |
| 2010/0316619 A1* | 12/2010 | Wittke ................... A23L 1/296 424/93.45 |
| 2012/0121561 A1 | 5/2012 | Mercenier et al. |
| 2012/0171166 A1 | 7/2012 | Chow |
| 2012/0172319 A1 | 7/2012 | Chow |
| 2012/0177691 A1 | 7/2012 | Stahl et al. |
| 2012/0294840 A1 | 11/2012 | Newburg et al. |
| 2013/0021472 A1 | 1/2013 | Newburg et al. |
| 2013/0059815 A1 | 3/2013 | Fournell et al. |
| 2014/0286908 A1 | 9/2014 | Garcia-Rodenas et al. |
| 2014/0335065 A1 | 11/2014 | Davis |
| 2015/0079040 A1 | 3/2015 | O'Neill et al. |
| 2016/0113976 A1 | 4/2016 | Burcelin et al. |
| 2018/0078589 A1 | 3/2018 | Kyle et al. |
| 2018/0110253 A1 | 4/2018 | Sprenger et al. |
| 2018/0200312 A1 | 7/2018 | Snijders et al. |
| 2018/0220691 A1 | 8/2018 | Garcia-Rodenas et al. |
| 2019/0069586 A1 | 3/2019 | Kyle et al. |
| 2019/0134114 A1 | 5/2019 | Kusuda et al. |
| 2019/0201459 A1 | 7/2019 | Koshida et al. |
| 2019/0224254 A1 | 7/2019 | Kyle et al. |
| 2019/0240268 A1 | 8/2019 | Koshida et al. |

FOREIGN PATENT DOCUMENTS

| | | | |
|---|---|---|---|
| CA | 2818505 | 11/2010 | |
| CA | 2822660 | 7/2012 | |
| CH | WO 2009077352 A1 * | 6/2009 | ........... A61K 31/702 |
| CN | 101909615 A | 12/2010 | |
| CN | 101909644 A | 12/2010 | |
| CN | 103797021 | 5/2014 | |
| EP | 1887017 | 2/2008 | |
| EP | 2072052 | 6/2009 | |
| EP | 1996031 B1 | 7/2009 | |
| EP | 2279672 | 2/2011 | |
| EP | 1609463 B1 | 5/2011 | |
| EP | 2429551 A1 | 3/2012 | |
| EP | 2455387 | 5/2012 | |
| EP | 2642876 A1 | 10/2013 | |
| EP | 2836223 A1 | 2/2015 | |
| EP | 2234627 B1 | 5/2016 | |
| EP | 2643004 B1 | 12/2016 | |
| EP | 2643005 B1 | 3/2017 | |
| EP | 2768311 B1 | 2/2018 | |
| EP | 3285785 A1 | 2/2018 | |
| EP | 3331383 A1 | 6/2018 | |
| EP | 3366299 A1 | 8/2018 | |
| EP | 3366300 A1 | 8/2018 | |
| EP | 3268019 A1 | 10/2018 | |
| EP | 3426270 A1 | 1/2019 | |
| EP | 3443969 A1 | 2/2019 | |
| EP | 3478082 A1 | 5/2019 | |
| EP | 3478093 A1 | 5/2019 | |
| EP | 2201955 B1 | 8/2019 | |
| EP | 3522894 A1 | 8/2019 | |
| EP | 3426269 A1 | 10/2019 | |
| WO | 2003/082313 | 10/2003 | |
| WO | 2004/041291 | 5/2004 | |
| WO | 2004052121 | 6/2004 | |
| WO | 2005/067962 | 7/2005 | |
| WO | 2005/122790 | 12/2005 | |
| WO | 2007/101675 | 9/2007 | |
| WO | 2007108690 | 9/2007 | |
| WO | 2009059996 | 5/2009 | |
| WO | 2009077352 | 6/2009 | |
| WO | 2010142504 | 12/2010 | |
| WO | 2011014468 | 2/2011 | |
| WO | 2012069415 | 5/2012 | |
| WO | 2012/076323 | 6/2012 | |
| WO | 2013185780 | 12/2013 | |
| WO | 2004047778 | 6/2014 | |
| WO | 2018106844 A1 | 6/2018 | |
| WO | 2018112366 A1 | 6/2018 | |
| WO | 2018169297 A1 | 9/2018 | |
| WO | 2018190407 A1 | 10/2018 | |
| WO | 2019055718 A1 | 3/2019 | |

OTHER PUBLICATIONS

Search Report and Written Opinion in SG 201305083-6 dated Dec. 2, 2014.
Search Report and Written Opinion in SG 2014013478 dated Apr. 6, 2015.
Office Action and Search Report in TW Application No. 100149846 dated Apr. 21, 2015.
Office Action in VN 1-2013-02056 dated May 25, 2015 (received Jul. 9, 2015).
Whorwell, et al., "Efficacy of an Encapsulated Probiotic Bifidobacterium infantis 35624 in Women with Irritable Bowel Syndrome," Am. J. of Gastroenterology, vol. 101, pp. 1581-1590 (2006).
Schmelzle et al., "Randomized double-blind study of the nutritional efficacy and bifidogenicity of a new infant formula containing partially hydrolyzed protein, a high beta-palmitic acid level, and nondigestible oligosaccharides," J. Pediatr. Gastroenterol. Nutr., vol. 36(3), pp. 343-351 (2003).
Schnabel, et al., "Gangliosides protect bowel in an infant model of necrotizing enterocolitis by suppressing proinflammatory signals," J. Pediatr. Gastroenter. Nutr., vol. 49, pp. 382-392 (2009).
Scholtens et al., "Bifodogenic effects of solid weaning foods with added prebiotic oligosaccharides: a randomised controlled clinical trial," J. Pediatr. Gatroenterol. Nutr., vol. 42(5), pp. 552-559 (2006).
Schrezenmeir et al., "Benefits of oral supplementation with and without synbiotics in young children with acute bacterial infections," Clin. Pediatr., vol. 43(3), pp. 239-249 (2004).
Sela et al., "The genome sequence of *Bifidobacterium longum* subsp. Infantis reveals adaptations for milk utilization within the infant microbiome," Proc. Natl. Acad. Sci., USA, vol. 105(48), p. 18964-18969 (2008).
Sela et al., "Nursing our microbiota: molecular linkages between bifidobacteria and milk oligosaccharides," Trends Microb., vol. 18(7), pp. 298-307 (2010).

(56) References Cited

OTHER PUBLICATIONS

Sherman et al., "Potential roles and clinical utitlity of prebiotics in newborns, infants, and children," Proceedings from a global prebiotic summit meeting, New York City, Jun. 27-28, 2008, J. Pediatr., vol. 155(5), pp. S61-S70 (2009).
Soitgiu et al., "Immunomodulation of fucosyl-lactose and lacto-N-fucopentaose on mononuclear cells from multiple sclerosis and healthy subjects," Inter. J. Biomediacl. Sci., vol. 2(2), pp. 114-120 (2006).
Soukup et al., "Role of monocytes and eosinophils in human RSV infection in vitro," Clinical Immunology, vol. 107, pp. 178-185(2003).
Spurrell, et al., "Human airway epithelial cells produce IP-10 (CXCL 10) in vitro and in vivo upon rhinovirus infection," Am. J. Physiol. Lung Cell Mol. Physiol., vol. 289, pp. L85-95 (2005).
Stevens, et al., "Glycan microarray analysis of the hemagglutinins from modern and pandemic influenza viruses reveals different receptor specificities," Journal of Molecular Biology, vol. 355, pp. 1143-1155 (2006).
Stevens et al., "Structure and receptor specificity of the Hemagglutinin from an H5N1 influenza virus," Science, vol. 312, pp. 404-410 (2006).
Stewart, et al., "Fructooliogosaccharides exhibit more rapid fermentation than long-chain inulin in an in vitro fermentation system," Nutr. Res., vol. 28, pp. 329-334 (2008).
Sun, X., "Recent anti-influenza strategies in multivalent sialyloigosaccharides and sialylmimetics approaches," Current Medicinal Chemistry, vol. 14, pp. 2304-2313 (2007).
Suzuki et al., "Receptor specificities of human respiroviruses," J. of Virol., vol. 75(10), pp. 4604-4613 (2001).
Szylit, et al., "Physiological and pathphysiological effects of carbohydrate fermentation," World Rev. Nutr. Diet., vol. 74, pp. 88-122 (1993).
Teneberg, et al., "Inhibition of nonopsonic Helicobacter pylori-induced activation of human neutrophils by sialylated oligosaccharides," Glycobiology, vol. 10(11), pp. 1171-1181 (2000).
Thurl, et al., "Variation of human milk oligosaccharides in relation to milk groups and lactational periods," Br. J. of Nutr., vol. 104(9), pp. 1261-1271 (2010).
Thurl, et al., "Variation of netural oligosaccharides and lactose in human milk during the feeding," Zeitschrift fuer Emaehrungswissenschaft, Steinkopf Verlag, Darmstadt, DE, vol. 32 (41), pp. 262-269 (1993).
Thymann et al., "Formula-feeding reduces lactose digestive capacity in neonatal pigs," British J. of Nutrition, vol. 95, pp. 1075-1081 (2006).
Tijerina-Saenz, "Antioxidant capacity of human milk and its association with vitamins A and E and fatty acid composition," Acta Paediatrica, vol. 98(11), pp. 1793-1798 (2009).
Tsopmo et al., "Human Milk has Anti-Oxidant Properties to Protect Premature Infants," Current Pediatric Reviews, vol. 3, pp. 45-51 (2007).
Vandenplas, Y., "Oligosaccharides in infant formula," Br. J. Nutr., vol. 87 (Suppl. 2), pp. S293-296 (2002).
Varki, et al., "Biological roles of oligosaccharides: all of the theories are correct," Glycobiology, vol. 3(2), pp. 97-130 (1993).
Veereman, G., "Pediatric applications of inulin and oligofructose," J. Nutr., vol. 137(11 Suppl.), pp. 2585S-2589S (2007).
Veereman-Wauters, G., "Application of prebiotics in infant foods," Br. J. Nutr., vol. 93 (Suppl. 1), pp. S57-60 (2005).
Vester Boler et al., "Carbohydrates blended with polydextrose lower gas production and short-chain fatty acid production in an in vitro system," Nutr. Res., vol. 29, pp. 631-639 (2009).
Videla et al., "Dietary inulin improves distal colitis induced by dextran sodium sulfate in the ratInulin in Dextran Sodium Sulfate Colitis," Am. J. of Gastro., vol. 96, pp. 1486-1493 (2001).
Von Nicolai et al., "Partial purification and properties of neuraminidase from Bifidobacterium lactentis," Hoppe Seylers Z Physiol. Chem., vol. 362(2), pp. 153-162 (1981).

Vos et al., "Dietary supplementation of neutral and acidic oligosaccharides enhances Th 1-dependent vaccination responses in mice," Pediatr. Allergy Immunol., vol. 18(4), pp. 304-312, (2007).
Vos et al., "Immune-modulatory effects and potential working mechanisms of orally applied nondigestible carbohydrates," Critical Reviews in Immunology, vol. 27(2), pp. 97-140 (Jan. 2007).
Wada, et al., "Bifidobacterium bifidum lacto-N-biosidase, a critical enzyme for the degradation of human milk oligosaccharides with a type 1 structure," Appl. Environ. Microbiol., vol. 74(13), pp. 3996-4004 (2008).
Walker, A., "Milk and two oligosaccharides," Nat. Rev. Microbiol., vol. 7(7), p. 483 (2009).
Wang et al., "Effects of the in vitro fermentation of oligofructose and inulin by bacteria growing in the human large intestine," J. Appl. Bacteriol., vol. 75, pp. 373-380 (1993).
Wang, et al., "The role and potential of sialic acid in human nutrition," European Journal of Clinical Nutrition, vol. 57 (11), pp. 1351-1369 (2003).
Ward, Robert E. et al., "In vitro fermentability of human milk oligosaccharides by several strains of bifidobacteria," Molecular Nutrition & Food Research, vol. 51 (11), Nov. 2007, pp. 1398-1405.
Ward et al., "In vitro fermentation of breast milk oliogsaccharides by Bifidobacterium infantis and Lactobacillus gasseri," Appl. Environ. Microbiol., vol. 72, pp. 4497-4499 (2006).
Westerbeek et al., "Design of a randomised controlled trial on immune effects of acidic and neutral oligosaccharides in the nutrition of preterm infants: carrot study," BMC Pediatr., vol. 23, pp. 8-46 (2008).
Westerbeek et al., "The effect of enteral supplementation of a prebiotic mixture of non-human milk galacto-, fructo-, and acidic oligosaccharides on intestinal permeability in preterm infants," Br. J. Nutr., vol. 105, pp. 268-274 (2011).
Wilson, M., "The gastrointestinal tract and its indigenous microbiota, Microbial Inhabitants of Humans: their ecology and role in health and disease," Cambridge University Press, pp. 283-287 (2005).
Wong, et al., "Colonic health: fermentation and short chain fatty acids," J. Clin. Gastroenterol., vol. 40(3), pp. 235-243 (2006).
Wu, et al., "Development of an Annotated Library of Neutral Human Milk Oligosaccharides," J. Proteome Res., vol. 9, pp. 4138-4151 (2010).
Xiao et al., "Distribution of in vitro fermentation ability of lacto-N-biose 1, a major building block of human milk oligosaccharides, in bifidobacterial strains," Appl. Environ. Microbiol., vol. 76(1), pp. 54-59 (2010).
Yamada, et al., "Lactotriaose-containing carbosilane dendrimers: Synthesis and lectin-binding activities," Bioorganic & Medicinal Chemistry, vol. 15(4), pp. 1606-1614 (2007).
Yamazaki et al., "Measurement of growth of bifidobacteria on inulofructosaccharides," Let. Appl. Microbiol., vol. 10, pp. 229-232(1990).
Yau, et al., "Effect of nucleotides on diarrhea and immune responses in healthy term infants in Taiwan,", J. Pediatr. Gastro. Nutr., vol. 36(1), pp. 37-43 (2003).
Yoshida et al., "Role of N-3 polyunsaturated fatty acids and sialic acid in learning performance of rats,", J. of Neurochemistry, vol. 65(Suppl.), p. S173 (1995).
Yu, et al., "Improved extraction of PCT-quality community DNA from digesta and fecal samples," BioTechniques, vol. 36, pp. 808-812 (2004).
Yuhas et al., "Human milk fatty acid composition from nine countries varies most in DHA," Lipids, vol. 41(9), pp. 851-858 (2006).
Grulee et al., "Breast and artificial feeding: influence of morbidity and mortality of twenty thousand infants," J. Am. Med. Assoc., vol. 103, pp. 735-738 (1934).
Gunnarsson et al., "Sialic acid residues play a pivotal role in alpha 1-acid glycoprotein (AGP)-induced generation of reactive oxygen species in chemotactic peptide pre-activated neutrophil granulocytes," Inflammation Research, vol. 59 (2), pp. 89-95 (2010).
Gutierrez et al., "Immune response to nucleotide-supplemented infant formulae: systematic review and meta-analysis," British J. of Nutr., (2007), 98 (Suppl. 1), S64-S67 (2007).

(56) References Cited

OTHER PUBLICATIONS

Hernot et al., "In vitro fermentation profiles, gas production rates, and microbiota modulation as affected by certain fructans, galactooligosaccharides, and polydextrose," J. Agric. Food Chem., vol. 57, pp. 1354-1361 (2009).
Hidaka, et al., "Effects of fructooligosaccharides on intestinal flora and human health," Bifidobacteria Microflora, vol. 5 (1), pp. 37-50(1986).
"Human Breast Milk," Wikipedia, last accessed Feb. 2, 2012.
Idota, et al., "Growth-promoting effects of N-Acetylneuraminic acid-containing substances on bifidobacterial," Biosci. Biotech. Biochem., vol. 58, pp. 1720-1722 (1994).
Issacs, "Human milk inactivates pathogens individually, additively, and synergistically," J. Nutr., vol. 135(5), pp. 1286-1288 (2005).
Jantscher-Krenn et al., "Human milk oligosaccharides and their potential benefits for the breast-fed neonate," Minerva Pediatr., vol. 64, pp. 83-99 (2012).
Jyonouchi et al., "Dietary ribonucleotides increase antigen-specific type 1 T-helper cells in the regional draining lymph nodes in young BALB/cJ mice," Nutrition, vol. 19(1), pp. 41-46 (2003).
Kanamori, et al., "Experience of long-term synbiotic therapy in seven short bowel patients with refractory enterocolitis," J. of Pediatric Surgery, vol. 39 (11), pp. 1686-1692 (2004).
Karimi et al., "Lactobacillus reuteri induced regulatory T cells protect against an allergic airway response in mice," Am. J. Resp. Crit. Care Med., vol. 179(3), pp. 186-193 (2009).
Kashyap, et al., "Growth Nutrient Retention and Metabolic Response of Low-birth-weight Infants fed Supplemented and Unsupplemented Preterm Human Milk," American Journal of Clinical Nutrition, American Society for Nutrition, U.S. vol. 52(2), pp. 254-262, (1990).
Kasson, et al., "Structural basis for influence of viral glycans on ligand binding by influenze hemagglutinin," Biophysical Journal, vol. 95(7), pp. L48-L50 (2008).
Kauth, et al., "Synergistically upregulated IL-10 production in cocultures of monocytes and T cells after stimulation with RSV," International Archives of Allergy and Immunology, vol. 142, pp. 116-126 (2007).
Kay, et al., "Mechanisms of T lymphocyte activation," Immunology Letters, vol. 29, pp. 51-54 (1991).
Khachik et al., "Identification, Quantification, and Relative Concentrations of Carotenoids and their Metabolites in Human Milk and Serum," Analytical Chemistry, American Chemical Society, US, vol. 69(10), pp. 1873-1881 (1997).
Kien, C.L., "Digestion, absorption, and fermentation of carbohydrates in the newborn," Clin. Perinatol., vol. 23(2), pp. 211-228 (1996).
Kitaoka et al., "Novel putative galactose operon involving lacto-N-biose phosphorylase in Bifidobacterium longum," Appl. Environ. Microbiol., vol. 71(6), pp. 3158-3162 (2005).
Kiyohara, et al., "An exo-{alpha}-sialidase from bifidobacteria involved in the degradation of sialyloliogosaccharides in human milk and intestinal glycoconjugates," Glycobiology, vol. 21(4), pp. 437-447 (2011).
Kiyohara et al., "Prebiotic effect of lacto-N-biose 1 on bifidobacterial growth," Biosci. Biotechnol. Biochem., vol. 73(5), pp. 1175-1179 (2009).
Knol, et al., "Colon microflora in infants fed formula and galacto- and fructo-oligosaccharides: more like breast-fed infants," J. Pediatr. Gastroenterol. Nutr., vol. 40(1), pp. 36-42 (2005).
Kobata, A. , "Structures and application of oligosaccharides in human milk," Proc. Jpn. Acad. Ser. B. Phys. Biol. Sci., vol. 86(7), pp. 731-747 (2010).
Kulkarni et al., "Influence of dietary nucleotide restriction on bacterial sepsis and phagocytic cell function in mice," Arch. Surg., vol. 121(2), pp. 169-172 (1986).
Kunz, C., "Komplexe Oligosaccharide in der Saeuglingsernaehrung," Monatsschrift Fuer Kinderheilkunde, Springer Verlag, DE, vol. 146(1), pp. 49-56 (1998).
Kunz et al., "Biological functions of oligosaccharides in human milk," Acta paediatr., vol. 82(11), pp. 903-912 (1993).
Kunz et al., "Oligosaccharides in human milk: structural, functional, and metabolic aspects," Annu. Rev. Nutr., vol. 20, pp. 699-722 (2000).
Kunz, et al., "Potential anti-inflammatory and anti-infectious effects of Human Milk Oligosaccharides," from Bioactive Components of Milk, Springer, pp. 455-465 (2008).
Kunze, et al., "Lactobacillus reuteri enhances excitability of colonic AH neurons by inhibiting calcium dependent potassium channel opening," J. Cell Mol. Med., vol. 13(8B), pp. 2261-2270 (2009).
Kuntz et al., "Oligosaccharides from human milk induce growth arrest via G2/M by influencing growth-related cell cycle genes in intestinal epithelial cells," Br. J. Nutr., vol. 101, pp. 1306-1315 (2009).
Kuntz, et al., "Oligosaccharides from human milk influence growth-related characteristics of intestinally transformed and non-transformed intestinal cells," Br. J. Nutr., vol. 99, pp. 462-471 (2008).
Kurokawa et al., "Comparative metagenomics revealed commonly enriched gene sets in human gut microbiomes," DNA Res., vol. 14, pp. 169-181 (2007).
Lara-Villoslada, "Oligosaccharides isolated from goat milk reduce intestinal inflammation in a rat model of dextran sodium sulfate-induced colitis," Clin. Nutr., vol. 25(3), pp. 477-488 (2006).
Leach et al., "Total potentially available nucleosides of human milk by stage of lactation," Am J. Clin. Nutr., vol. 61(6), pp. 1224-1230 (1995).
Lee et al., "Genomic insights into bifidobacteria," Microbiol. Mol. Biol. Rev., vol. 74(3), pp. 378-416 (2010).
Leyer, et al., "Probiotic Effects on Cold and Influenza-Like Symptom Incidence and Duration in Children," Pediatrics, vol. 124(2), pp. e172-e179 (2009).
Lin et al., "Necrotizing Enterocolitis: Recent Scientific Advances in Pathophysiology and Prevention," Seminars in Perinatology, WB Saunders, GB, vol. 32(2), pp. 70-82 (Mar. 14, 2008).
LoCascio, et al., "A versatile and scalable strategy for glycoprofiling bifidobacterial consumption of human milk oligosaccharides," Microb. Biotechnol., vol. 2, pp. 333-342 (2009).
LoCascio et al., "Broad conservation of milk utilization genes in *Bifidobacterium longum* subsp. Infantix as revealed by comparative genomic hybridization," Appl. Environ. Microbiol., vol. 76(22), pp. 7373-7381 (2010).
LoCascio et al., "Glycoprofiling of bifidobacterial consumption of human milk oligosaccharides demonstrates strain specific, preferential consumption of small chain glycans secreted in early human lactation," J. Agric. Food Chem., vol. 55(22), pp. 8914-8919 (2007).
Ma et al., "Live Lactobacillus reuteri is essential for the inhibitory effect of tumour necrosis factor alpha-induced interleukin-8 expression," Infect. Immun., vol. 72, pp. 5308-5314 (2004).
Maaheimo, "Synthesis of a divalent sialyl Lewis X-O-glycan, a potent inhibitor of lymphocyte-endothelium adhesion. Evidence that multvalency enhances the saccharide binding to selectins," European Journal of Biochemistry, vol. 234, pp. 616-625 (1995).
Macfarlane et al., "Bacterial metabolism and health-related effects of galcto-oligosaccharides and other prebiotics," J. Appl. Microbiol., vol. 104(2), pp. 305-344 (2008).
MacIver, et al., "Glucose metabolism in lymphocytes is a regulated process with significant effects on immune cell function and survival," J. Leukoc. Biol., vol. 84, pp. 949-957 (2008).
Magne et al., "Effects on faecal microbiota of dietary and acidic oligosaccharides in children during partial formula feeding," J. Pediatr. Gastroenterol. Nutr., vol. 46(5), pp. 580-588 (2008).
Malhotra, et al., "Isolation and characterisation of potential respiratory syncytial virus receptor(s) on epithelial cells," Microbes and Infection, vol. 5, pp. 123-133 (2003).
Marcobal, et al, "Consumption of human milk oligosaccharides by gut-related microbes," J. Agric. Food Chem., vol. 58, pp. 5334-5340 (2010).
Mariat, "The Firmicutes/Bacteroidetes ratio of the human microbiota changes with age," BMC Microbiol., vol. 9, p. 123 (2009).

(56) References Cited

OTHER PUBLICATIONS

Marlett et al., "American Dietetic Association, Position of the American Dietetic Association: health implications of dietary fiber," J. Am. Diet. Assoc., vol. 102(7), pp. 993-1000 (2002).
Non final rejection for U.S. Appl. No. 13/334,933 dated Jun. 27, 2014.
First Examination Report in NZ 611,807 dated Dec. 19, 2013 received Jun. 16, 2014.
Amendment for U.S. Appl. No. 13/334,933 dated Sep. 29, 2014.
Office Action for U.S. Appl. No. 13/334,933 dated Oct. 27, 2014.
Response with RCE for U.S. Appl. No. 13/334,933 dated Jan. 27, 2015.
First Office Action in CN 201180067021.x (PCT/US2011/067018) dated Aug. 15, 2014.
First Office Action in CN 201180068703.2 dated Nov. 4, 2014.
Office Action in EP Application No. 11811266.3 dated Aug. 18, 2014.
First Examination Report in NZ 620,311 dated Nov. 3, 2014.
First Examination Report in NZ 621,603 dated Nov. 28, 2014.
Written Opinion in SG 2013050067 dated Aug. 12, 2014.
Asakuma et al., "Variation of major neutral oligosaccharides levels in human colostrum", European Journal of Clinical Nutrition, vol. 62, pp. 488-494 Mar. 21, 2007.
Bode et al., "Human milk oligosaccharides prevent Nectrotizing Enterocolitis in neonatal rats," The FASEB Journal, vol. 24, p. 206.3 Apr. 2010.
Sumiyoshu W. et al., "Determination of each neutral oligosaccharide in the milk of Japanese women during the course of lactation," Br. J. Nutr. vol. 89, pp. 61-69 Mar. 9, 2003.
Urashima, Tadasu et al., "Biological significance of human milk oligosaccharides," Milk Science, vol. 56(4), pp. 155-176 (2008).
Office Action for U.S. Appl. No. 13/335,341 dated Nov. 5, 2014.
Procter & Gamble Bifantis news release dated May 12, 2009 (4 pages).
Response in U.S. Appl. No. 13/335,341 dated Feb. 3, 2015.
Office Action in CA 2,846,603 dated Feb. 3, 2015.
Third Party Observations from EP Application No. 12766344.1 dated Jan. 5, 2015.
Office Action for EP Application No. 12766344.1 dated Jan. 27, 2015.
Office Action for EP Application No. 12741201.3 dated Jan. 12, 2015.
Office Action for U.S. Appl. No. 13/334,933 dated Mar. 23, 2015.
Office Action in CA 2,842,672 dated Feb. 23, 2015.
First Office Action in CN 201180046188.2 dated Feb. 17, 2015.
Search Report and Written Opinion in SG 201400490.7 dated Mar. 16, 2015.
Ziegler, et al., "Term infants fed formula supplemented with selected blends of prebiotics grow normally and have soft stools similar to those reported for breast-fed infants," J. Pediatr. Gastroenterol. Nutr., vol. 44, pp. 359-364 (2007).
Zivkovic et al., "Microbes and health sackler colloquium: Human mild glycobiome and its impact on the infant gastrointestinal microbiota," Proc. Natl. Acad. Sci., USA (2010).
Final Office Action in U.S. Appl. No. 13/334,933 dated Aug. 10, 2015.
Amendment with RCE in U.S. Appl. No. 13/334,933 dated Nov. 10, 2015.
Office Action for U.S. Appl. No. 13/334,933 dated Jan. 22, 2016.
Amendment with RCE in U.S. Appl. No. 13/335,341 dated Sep. 4, 2015.
Office Action for U.S. Appl. No. 13/335,341 dated Oct. 7, 2015.
Amendment for U.S. Appl. No. 13/335,341 dated Feb. 8, 2016.
Office Action in CA 2,846,603 dated Oct. 26, 2015.
Office Action in CA 2,842,672 dated Dec. 1, 2015.
English translation of Second Office Action in CN 201180067021.x dated Jun. 26, 2015.
English translation of Third Office Action in CN 201180067021.x dated Jan. 8, 2016.
English translation of Notification of Grant of Patent in CN201180068703.2 dated Jul. 15, 2015.
English translation of Second Office Action in CN 201280051863.0 dated Nov. 4, 2015.
English summary of Office Action in MX/a/2013/007675 dated Oct. 30, 2015.
Search Report and Written Opinion in SG 201305083-6 dated Jul. 31, 2015.
Written Opinion in SG 2014013478 dated Dec. 22, 2015.
English translation of Rejection of TW Application No. 100149846 dated Dec. 18, 2015.
English translation of Office Action in TW Application No. 100150004 dated Aug. 25, 2015.
Chen, L.R., "Introduction of Oligosaccharide," Department of Dietetics, MacKay Memorial Hospital, Oct. 2002, http://www.mmh.org.tw/nutrition/nutrroom/26loligo.htm.
Chou, J.J., "Microorganisms, Foods, Probiotics, and Bifidus," Food and Life, Dec. 2004 http;//203.145.193.110/NSC_INDEX/Journal/EJ0001/9312/9312-02.pdf.
Oliveros et al., "Prebioticos en formulas infantiles," An Pediatr., Monograph 4(1) 20-29 (Apr. 2006).
Procter & Gamble "What is Bifantis ?" About Bifantis, Nov. 4, 2010 https://web.archive.org/web/20101104124637/http://www.bifantis.com.
Martin-Sosa, et al., "Sialyloligosaccharides in human and bovine milk and in infant formulas: variations with the progression of lactation," J. Dairy Sci., vol. 86, pp. 52-59 (2003).
Martinez-Ferez, et al., "Goats' milk as a natural source of lactose-derived oligosaccharides: Isolation by membrane technology," Intern. Dairy J., vol. 16(2), pp. 173-181 (2006).
Masuko, et al., "Carbohydrate analysis by a phenol-sulfuric acid method in microplate format," Anal. Biochem., vol. 339, pp. 69-72 (2005).
McKeller et al., "Metabolism of fructo-oligosaccharides by *Bifidobacterium* spp.," Appl. Microbiol. Biotechnol., vol. 31, pp. 537-541 (1989).
McVeagh, et al., "Human milk oligosaccharides: only the breast," J. Paediatr. Child Health, vol. 33(4), pp. 281-286 (1997).
Meinzen-Derr, "Role of human milk in extremely low birth weight infants' risk of necrotizing enterocolitis or death," J. Perinatology, vol. 29, pp. 57-62 (2009).
Michalek, et al., "Cutting Edge: Distinct Glycolytic and Lipid Oxidative Metabolic Programs are Essential for Effector and Regulatory CD4+T Cell Subsets," Journal of Immunology, vol. 186, pp. 3299-3303 (2011).
Miniello et al., "Prebiotics in infant milk formulas: new perspectives," Acta Paediatr. Suppl., vol. 91(441), pp. 68-76 (2003).
Miwa, et al., "Cooperation of beta-galactosidase and beta-N-acetylhexosaminidase from bifidobacteria in assimilation of human milk oligosaccharides with type 2 structure," Glycobiology, vol. 20(11), pp. 1402-1409 (2010).
Monaco et al., "The addition of polydextrose and galactooliogssacharide to formula does not affect barrier function or bacterial translocation in neonatal piglets," FASEB Journal, Meeting Abstract Supplement, vol. 23: LB479 (2009).
Moro et al., "Dosage-related bifidogenic effects of galacto- and fructooligosaccharides in formula-fed term infants," J. Pediatr. Gastroenterol. Nutr., vol. 34(3), pp. 291-295 (2002).
Moro et al., "Effects of a new mixture of prebiotics on faecal flora and stools in term infants," Acta Paediatr. Suppl., vol. 91(441), pp. 77-79 (2003).
Moro, et al., "Reproducing the bifidogenic effect of human milk in formula-fed infants: shy and how ?", Acta Paediatr. Suppl., vol. 94(449), pp. 14-17 (2005).
Morrow et al., "Human milk oligosaccharides are associated with protection against diarrhea in breast-fed infants," J. Pediatr., pp. 297-303 (2004).
Morrow et al., "Novel salivary and genetic biomarkers of risk for NEC or death in premature infants," FASEB, vol. 23 (Meeting Abstract Supplement), LB270 (2009).
Morrow et al., "Secretor phenotype and genotype are novel predictors of severe outcomes in premature infants," FASEB, vol. 24 (Meeting Abstract Supplement), p. 480.6 (2010).

(56) References Cited

OTHER PUBLICATIONS

Mountzouris et al., "Intestinal microflora of human infants and current trends for its nutritional modulation," Br. J. Nutr., vol. 87(5), pp. 405-420 (2002).
Mshvildadze et al., "Probiotics and prevention of necrotizing enterocolitis," Early Human Development, Shannon, IR, vol. 85(10), pp. S71-S74 (Oct. 1, 2009).
Nakhla et al., "Neutral oligosaccharide content of preterm human milk," Br. J. Nutr., vol. 82, pp. 361-367 (1999).
Nakamura et al., "Concentrations of sialyloligosaccharides in bovine colostrum and milk during the prepartum and early lactation," J. Dairy Sci., vol. 86, pp. 1315-1320 (2003).
Nakamura et al., "Molecular ecological analysis of fecal bacterial populations from term infants fed formula supplemented with selected blends of prebiotics," Appl. Environ. Microbiol., vol. 75, pp. 1121-1128 (2009).
Nakano et al., "Sialic acid in human milk," Acta paediatrica taiwanica, vol. 42(1), pp. 11-17 (2001).
Navarro, et al., "Influence of Dietary Nucleotides on Plasma Immunoglobulin Levels and Lymphocyte Subsets of Preterm Infants," Biofactors, vol. 10(1), pp. 67-76 (1999).
Newburg, DS, "Neonatal protection by an innate immune system of human milk consisting of oligosaccharides and glycans," J. Anim. Sci., vol. 87 (13 Suppl.), pp. 26-34 (2009).
Newburg, et al., "Human milk glycans protect infants against enteric pathogens," Annu. Rev. Nutr., vol. 25, pp. 37-58 (2005).
Newburg, et al., "Innate protection conferred by fucosylated oligosaccharides of human milk against diarrhea in breastfed infants," Glycobiology, vol. 14(3), pp. 253-263 (2004).
Newburg, et al. "Oligosaccharides in human milk and bacterial colonization," J. Pediatr. Gasterenterol. Nutr., vol. 30, pp. S8-S17 (2000).
Newburg, et al., "Protection of the neonate by the innate immune system of developing gut and of human milk," Ped. Res., vol. 61(1), pp. 2-8 (2007).
Nicholls et al., "Evolving complexities of influenza virus and its receptors," Trends in Microbiology, vol. 16(4), pp. 149-157 (2008).
Ninonuevo et al., "A strategy for annotating the human milk glycome," J. Agric. Food Chem., vol. 54, pp. 7471-7480 (2006).
Ninonuevo et al., "Mass spectrometric methods for analysis of oligosaccharides in human milk," Nutr. Rev., vol. 67 (Suppl. 2), pp. S216-S226 (2009).
Palmer et al., "Development of the human infant intestinal microbiota," Plos Biol., vol. 5, p.e. 177, pp. 1556-1573 (2007).
Parrett, et al., "In vitro fermentation of carbohydrate by breast fed and formula fed infants," Arch. Dis. Childhood, vol. 76, pp. 249-253 (1997).
Petschow et al., "Response of bifidobacterium species to growth promoters in human and cow milk," Pediatr. Res., vol. 29(2), pp. 208-213 (1991).
Pickering et al., "Modulation of the Immune System by Human Milk and Infant Formula Containing Nucleotides," Pediatrics, vol. 101(2), pp. 101(2), pp. 242-249 (1998).
Portelli, et al., "Effect of compounds with antibacterial activities in human milk on respiratory syncytial virus and cytomegalovirus in vitro," J. Med. Microbiol., vol. 47, pp. 1015-1018 (1998).
Probert et al., "Polydextrose, lactitol, and fructo-oligosaccharide fermentation by colonic bacteria in a three-stage continuous culture system," Appl. Environ. Microbiol., vol. 70(8), pp. 4505-4511 (2004).
Rinne, et al., "Similar bifidogenic effects of prebiotic-supplemented partially hydrolyzed infant formula and breastfeeding on infant gut microflora," Fems Immunology and Medical Microbiology, Elsevier Science BV, Amsterdam, NL, vol. 43(1), pp. 59-65 (2005).
Rivero-Urgell et al., "Oligosaccharides: application in infant food," Early Human Dev., vol. 65(Suppl.), pp. S43-S52 (2001).
Robertfroid, M., "Prebiotics: the concepts revisited," J. Nutr., vol. 137, pp. 830S-837S (2007).
Rueda et al., "Influence of dietary compounds on intestinal immunity," Microbiol. Ecol. Health Diseases, vol. 2, pp. 146S-156S (2000).
Rumessen, JJ., "Fructose and related food carbohydrates. Sources, intake, absorption, and clinical implications," Scand. J. Gastroenterol., vol. 27(10), pp. 819-828 (1992).
Russ et al., "Post-weaning effects of milk and milk components on the intestinal mucosa in inflammation," Mutation Research, Elsevier, Amsterdam, vol. 690, Nos. 1-2, Aug. 7, 2010, pp. 64-70.
Rycroft et al., "A comparative in vitro evaluation of the fermentation properties of prebiotic oligosaccharides," J. Appl. Microbiol., vol. 91, pp. 878-887 (2001).
Saedisomeolia et al., "Lycopene enrichment of cultured epithelial cells decreases the inflammation induced by rhinovirus infection and lipopolysaccharide," J. Nutritional Biochemistry, vol. 20, pp. 577-585 (2009).
Salminenen et al., "Microbial-host interactions: selecting the right probiotics and prebiotics for infants," Nestle Nutr. Workshop Ser. Pediatr. Program, vol. 64, pp. 201-213 (2009).
Sangwan, et al., "Galactooliogosaccharides: novel components of designer foods," J. of Food Science, vol. 76(4), pp. R103-R111 (May 2011).
Schaefer et al., "Ammonia saturation constants for predominant species of rumen bacteria." J. Dairy Sci., vol. 63(8), pp. 1248-1263 (1980).
Schaller et al., "Effect of Dietary Ribonucleotides on Infant Immune Status. Part 1: Humoral Responses," Pediatric Research, vol. 56(6), pp. 883-890 (2004).
Amendment for U.S. Appl. No. 13/335,341 dated Nov. 1, 2016.
Office Action for U.S. Appl. No. 13/335,341 dated Feb. 16, 2017.
Amendment in U.S. Appl. No. 14/238,822 dated Dec. 30, 2016.
Final Rejection for U.S. Appl. No. 14/238,822 dated Mar. 1, 2017.
Office Action in CA 2,846,603 dated Feb. 8, 2017.
Office Action in CA 2,842,672 dated Oct. 24, 2016.
Notice of Reexamination in CN 201280046188.2 dated Mar. 13, 2017.
Fourth Office Action in CN 201280051863.0 dated Dec. 15, 2016.
Exam Report Stage II for ID Application No. P00201400846 dated Feb. 24, 2017.
Exam Report Stage II for ID Application No. P00201401703 dated Mar. 9, 2017.
Third Office Action in MX/a/2013/007675 dated Mar. 7, 2017.
Office Action in MX/a/2014/000895 dated Mar. 7, 2017.
Substantive Examination Adverse Report in MY Application No. PI2013002504 dated Jan. 31, 2017.
Substantive Examination Adverse Report in MY Application No. PI2013002514 dated Jan. 31, 2017.
Substantive Examination Report in PH 1/2013/501382 dated Mar. 10, 2017.
Written Opinion in SG 2014004907 dated Nov. 3, 2016.
Office Action and Search Report in TW Application No. 101126368 dated May 4, 2016.
Decision on Rejection in TW Application No. 101126368 dated Dec. 28, 2016.
Amendment for U.S. Appl. No. 13/335,341 dated Jun. 16, 2017.
Office Action for U.S. Appl. No. 13/335,341 dated Oct. 3, 2017.
Office Action for U.S. Appl. No. 14/238,822 dated Sep. 29, 2017.
Office Action in CA 2,842,672 dated May 29, 2017.
Office Action in CA 2,822,660 dated Oct. 4, 2017.
Office Action in CA 2,822,219 dated Dec. 18, 2017.
Fifth Office Action in CN 201280051863.0 dated Jul. 4, 2017.
Exam Report for ID Application No. W00201302959 dated Jun. 8, 2017.
Office Action from Israeli Application No. 230892 dated Jan. 4, 2018.
Fourth Office Action in MX/a/2013/007675 dated Jul. 27, 2017.
Office Action in MX/a/2014/002491 dated Nov. 21, 2017.
Substantive Examination Adverse Report in MY Application No. PI2014000552 dated May 15, 2017.
Written Opinion in SG 2014004907 dated May 29, 2017.
Exam Report in SG 2014004907 dated Nov. 12, 2017.

(56) References Cited

OTHER PUBLICATIONS

Barbara et al., "Interactions Between Commensal Bacteria and Gut Sensorimotor Function in Health and Disease," American Journal of Gastroenterology, pp. 2560-2568, 2005.
Amendment from U.S. Appl. No. 14/238,822 dated Jan. 29, 2018.
Kim,"Short-Chain Fatty Acids in Ulcerative Colitis," Nutrition Reviews, Jan. 1998, pp. 17-24.
Office Action from U.S. Appl. No. 14/238,822 dated Apr. 12, 2018.
Non Final Office Action for U.S. Appl. No. 13/334,904 dated Jun. 27, 2014.
Amendment in U.S. Appl. No. 13/334,904 dated Sep. 29, 2014.
Final Office Action for U.S. Appl. No. 13/334,904 dated Nov. 18, 2014.
Response with RCE for U.S. Appl. No. 13/334,904 dated Feb. 18, 2015.
Office Action in U.S. Appl. No. 13/334,904 dated Mar. 20, 2015.
Response with RCE for U.S. Appl. No. 13/334,904 dated Jun. 22, 2015.
Final Office Action for U.S. Appl. No. 13/334,904 dated Jul. 24, 2015.
Remarks for Pre-Appeal Review for U.S. Appl. No. 13/334,904 dated Oct. 23, 2015.
Notice of Panel Decision from Pre-Appeal Brief Review in U.S. Appl. No. 13/334,904 dated Nov. 23, 2015.
Office Action in U.S. Appl. No. 13/334,904 dated Dec. 10, 2015.
Amendment in U.S. Appl. No. 13/334,904 dated Jun. 10, 2016.
Final Office Action in U.S. Appl. No. 13/334,904 dated Jul. 11, 2016.
Non-Final Office Action in U.S. Appl. No. 13/334,904 dated Jan. 25, 2017.
Office Action from Canadian Patent Application No. 2,822,497 dated Dec. 11, 2017.
First Office Action for CN Application No. 201180068712.1 dated Sep. 15, 2014.
Second Office Action for CN Application No. 201180068712.1 dated May 29, 2015.
English translation of Third Office Action for CN Application No. 201180068712.1 dated Dec. 8, 2015.
English translation of Fourth Office Action for CN Application No. 201180068712.1 dated Jun. 27, 2016.
Fifth Office Action for CN Application No. 201180068712.1 dated Apr. 1, 2017.
Office Action from Chinese Application No. 201180068712.1 dated Oct. 23, 2017.
Office Action in EP Application No. 11813500.3 dated Aug. 8, 2014.
Office Action in EP Application No. 11813500.3 dated Apr. 20, 2016.
Office Action in EP Application No. 11813500.3 dated Jul. 31, 2017.
Extended Search Report for EP Application No. 18153075.9 dated Apr. 5, 2018.
Exam Report for ID Application No. P00201401703 dated Mar. 15, 2018.
Exam Report Stage II for ID Application No. W00201302799 dated Mar. 13, 2018.
Exam Report Stage II for ID Application No. W00201302800 dated Feb. 27, 2018.
Exam Report Stage I for ID Application No. W00201302694 dated Apr. 16, 2018.
Office Action in MX Application No. MX/a/2013/007681.
Second Office Action in MX Application No. MX/a/2013/007681 dated Nov. 9, 2015.
Third Office Action in MX Application No. MX/a/2013/007681 dated Jun. 26, 2015.
Kamm, "Why the enteric nervous system is important to clinicians", GUT, vol. 47, No. 9004, Dec. 1, 2000, pp. 8iv-9.
Henningsson et al., "Short-Chain Fatty Acid Formation at Fermentation of Indigestible Carbohydrates," Naringsforskning, vol. 45, No. 1, Dec. 1, 2001, pp. 165-168.
Office Action in MY Application No. PI2013002501 dated Apr. 14, 2017.
Exam Report for NZ Application No. 612,504 dated Dec. 24, 2013.
Search Report and Written Opinion for SG 201305009-1 dated Nov. 4, 2014.
Written Opinion for SG 201305009-1 dated May 19, 2015.
Examination Report for SG 201305009-1 dated Jan. 12, 2016.
Office Action for TW 100149994 dated May 11, 2017.
Office Action for VN 1-2013-01948 dated May 25, 2015.
Nezami et al., "Enteric Nervous System in the Small Intestine: Pathophysiology and Clinicl Implications," Current Gastroenterology Reports, vol. 12, No. 5, Oct. 20, 2010, pp. 358-365.
Bertino et al., "Effects of Holder Pasteurization on Human Milk Oligosaccharides," International J. Immunopathol. (2008), 21(2), pp. 381-385.
Chu et al., "Role of Se-Dependent Glutathoine Peroxidases in Gastrointestinal Inflammation and Cancer," Free Radical Biol. & Med., 2005, 36(12), p. 1481-1495.
Friel, et al., "Evidence of Oxidative Stress in Full-Term Healthy Infants," Pediatric Research (2004), vol. 56, pp. 878-882.
Goedhart et al., "The Composition of Human Milk as a Model for the Design of Infant Formulas: Recent Findings and Possible Applications," Nutr. Res. Rev., (1994), 7, pp. 1-23.
Lawrence, RA, "Storage of Human Milk and the Influence of Procedures on Immunological Components of Human Milk," Acta Paediatr. Suppl., Aug. 1999, vol. 88, No. 430.
Ruiz-Palacios et al., "Campylobacter jejuni Binds Intestinal H(O) Antigen, and Fucosyloligosaccharides of Human Milk Inhibit its Binding and Infection" J. Biol. Chem., 2003, 278(16), p. 14112-14120.
Sandin, et al., "Faecal Short Chain Fatty acid Pattern and Allergy in Eady Childhood," ACTA Paediatrica, vol. 98, No. 6, May 1, 2009, pp. 823-827.
Schanler et al., "Randomized Trial of Donor Human Milk Versus Preterm Formula as Substitutes for Mothers' Own Milk in the Feeding of Extremely Premature Infants," Pediatrics, 2005, 116(2), pp. 400-406.
Schmelzle et al., "Randomized double-blind study of the nutritional efficacy and bifidogenicity of a new infant formula containing partially hydrolyzed protein, a high beta-palmitic acid level, and nondigestible oligosaccharides," J. Pediatr. Gastroenterol. Nutr., vol. 36(3), pp. 343-351.
Shen et al., "High-Performance Capillary Electrophoresis of Sialylated Oligosaccharides of Human Milk," Anal. Biochem., (2000), 279, pp. 37-45.
Walker, A., "Breast Milk as the Gold Standard for Protective Nutrients," J. Pediatrics, 2010, 156, p. S3-S7, available online Jan. 21, 2010.
Wood, Enteric nervous system, serotonin, and the irritable bowel syndrome, Current Opinion in Gastroenterology, Jan. 2001, vol. 17, No. 1, pp. 91-97.
Office Action from Canadian Patent Application No. 2,822,497 dated Sep. 26, 2018.
Office Action in CA 2,822,660 dated Jan. 28, 2019.
Reexamination Decision from Chinese Application No. 201180068712.1 dated Oct. 10, 2018.
Office Action in EP Application No. 11813500.3 dated Jan. 8, 2019.
Office Action in MX/a/2014/002491 dated Jul. 30, 2018.
Office Action in VN 1-2013-02056 dated Nov. 19, 2018.
Anonymous, "Guidelines for the Evaluation of Probiotics in Food", Joint FAQ/WHO Working Group Report on Drafting Guidelines for the Evaluation of Probiotics in Food, Food and Agriculture Organization of the United Nations and the World Health Organization, London, Ontario, Canada, Apr. 30 and May 1, 2002.
Buhner et al., "Activation of Human Enteric Neurons by Supernatants of Colonic Biopsy Specimens from Patients with Irritable Bowel Syndrome," Gastroenterology 2009, vol. 137, pp. 1425-1434.
Wood, "Enteric Neuroimmunophysiology and Pathophysiology" Gastroenterology 2004, vol. 127, No. 2, pp. 635-657.
Office Action for U.S. Appl. No. 13/335,341 dated Mar. 21, 2019.
Amendment from U.S. Appl. No. 14/238,822 dated Sep. 12, 2018.
Amendment for U.S. Appl. No. 15/401,488 dated Apr. 15, 2019.
Response to Office Action for U.S. Appl. No. 15/791,052 dated Apr. 10, 2019.
Office Action in CA 2,822,219 dated Mar. 12, 2019.

(56) References Cited

OTHER PUBLICATIONS

"Practical Inflammation Manual", pp. 2 to 7, with English Translation.
Response to Office Action from U.S. Appl. No. 14/238,822 dated May 13, 2019.
Office Action in CA 2,842,672 dated Apr. 8, 2019.
English translation of First Office Action in CN 201610935257.5 dated Apr. 9, 2019.
Office Action in MX/a/2014/002491dated Mar. 14, 2019.
Office action in MX/A/2013/007692 dated Apr. 11, 2019.
Office Action from Canadian Patent Application No. 2,822,497 dated Apr. 29, 2019.
Office Action for U.S. Appl. No. 13/335,341 dated Jun. 26, 2018.
Amendment for U.S. Appl. No. 13/335,341 dated Sep. 26, 2018.
Advisory Action for U.S. Appl. No. 13/335,341 dated Oct. 30, 2018.
Amendment for U.S. Appl. No. 13/335,341 dated Nov. 26, 2018.
Office Action from U.S. Appl. No. 14/238,822 dated Jan. 11, 2019.
Amendment for U.S. Appl. No. 15/401,488 dated Aug. 8, 2018.
Office Action for U.S. Appl. No. 15/401,488 dated Nov. 13, 2018.
Office Action for U.S. Appl. No. 15/791,052 dated Dec. 6, 2018.
Office Action in CA 2,842,672 dated Aug. 3, 2018.
Office Action in CA 2,822,219 dated Aug. 7, 2018.
Exam Report from Indian Application No. 5653/DELNP/2013 dated Mar. 15, 2018.
Office Action in MX/A/2013/007692 dated Nov. 7, 2018.
Substantive Examination Adverse Report in MY Application No. PI2013002514 dated Jul. 31, 2018.
Office Action for TW 100149994 dated Nov. 28, 2018.
Coppa et al., "Human Milk Oligosaccharides Inhibit the Adhesion to Caco-2 Cells of Diarrheal Pathogens: *Escherichia coli*, Vibrio cholerae, and *Salmonella fyris*," Pediatric Research, vol. 59, No. 3, 2006, pp. 377-382.
Saugstad, "Oxidative Stress in the Newborn—a 30-Year Perspective," Biol Neonate 2005, Vo. 88, pp. 228-236.
Amendment for U.S. Appl. No. 13/335,341 dated Jul. 22, 2019.
Office Action from U.S. Appl. No. 14/238,822 dated May 31, 2019.
Response to Office Action from U.S. Appl. No. 14/238,822 dated Sep. 3, 2019.
Notice of Allowance for U.S. Appl. No. 15/401,488 dated Aug. 21, 2019.
Office Action for U.S. Appl. No. 15/791,052 dated Jul. 17, 2019.
Decision on Rejection in CN 201711012480.3 dated Jul. 18, 2019.
Substantive Examination Adverse Report in MY Application No. PI2017000647 dated May 21, 2019.
Avery "Molecular Targets of Oxidative Stress," Biochem J., 2011, vol. 424, pp. 201-210.
Yaping et al., Feeding Tolerance of Premature Babies, "All-Sided Strategies of Home Nursing of Premature Babies", Huazhong University of Science and Technology, the 1st edition of Feb. 2009, pp. 85-87—English Abstract.
Office Action for U.S. Appl. No. 13/335,341 dated Oct. 24, 2019.
Office Action in CA 2,822,219 dated Nov. 20, 2019.
Office action in MX/A/2013/007692 dated Nov. 7, 2019.
Office Action in MY Application No. PI2013002501 dated Sep. 13, 2019.
Second Office Action in ON 201711012480.3 dated Oct. 18, 2019.
Response to Office Action for U.S. Appl. No. 15/791,052 dated Nov. 18, 2019.
Office Action for U.S. Appl. No. 15/791,052 dated Dec. 11, 2019.
Notice of Allowance for U.S. Appl. No. 14/238,822 dated Jan. 8, 2020.
Office Action in CA 2,842,672 dated Feb. 25, 2020.
Office Action in CA 2,822,660 dated Feb. 27, 2020.
Substantive Exam Report in MY Application No. PI 2014000183 dated Mar. 12, 2020.
Amendment for U.S. Appl. No. 13/335,341 dated Mar. 24, 2020.
Response to Office Action for U.S. Appl. No. 15/791,052 dated Mar. 11, 2020.
Office Action for U.S. Appl. No. 13/335,341 dated May 14, 2020.
Office Action for U.S. Appl. No. 15/791,052 dated Jun. 8, 2020.
Decision on Rejection from Chinese Application No. 201711012480.3 dated Mar. 11, 2020.
Amendment for U.S. Appl. No. 13/335,341 dated Aug. 14, 2020.
Office Action for U.S. Appl. No. 16/680,054 dated Aug. 11, 2020.
Office Action for U.S. Appl. No. 16/698,422 dated Aug. 11, 2020.
English translation of Notice of Reexamination in CN 201280051863.0 dated Jul. 8, 2020.
Communication pursuant to Article 94(3) EPC from EP Application 18153075.9 dated Aug. 24, 2020.
Response to Office Action for U.S. Appl. No. 15/791,052 dated May 18, 2021.
Notices of Opposition in EP Application No. 11813500.3 dated Mar. 9, 2021.
Notices of Opposition in EP Application No. 11813500.3 dated Mar. 16, 2021.
Chen et al., "Sterile inflammation: sensing and reacting to damage",Nat Rev Immunol, vol. 10, No. 12, 2010; 10:826-837.
Ioannidis et al., "Nutritional Modulation of the Inflammatory Bowel Response," Digestion 2011 84, pp. 89-101.
Kruidenier et al., "Review article : oxidative stress as a pathogenic factor in inflammatory bowel disease—radicals or ridiculous". Aliment Pharmacol Ther 2002; 16:1997-2015.
Medzhitov "Origin and Physiological Roles of Inflammation" Insight Review, vol. 454, Jul. 2008, pp. 428-435.
Rezaie et al., "Oxidative Stress and Pathogenesis of Inflammatory Bowel Disease: An Epiphenomenon or the Cause?" Dig Dis Sic (2007) 52: 2015-2011.
Traber et al., "Vitamins C and E: Beneficial Effects From a Mechanistic Perspective" Free Radic Biol Med. Sep. 1, 2011, 51(5) pp. 1000-1013.
Vegge et al., Clin. Nut. Supp., 2010, 5(2), PP422—published Sep. 5, 2010.
Office Action for U.S. Appl. No. 13/335,341 dated Dec. 4, 2020.
Response to Office Action for U.S. Appl. No. 15/791,052 dated Nov. 9, 2020.
Office Action for U.S. Appl. No. 15/791,052 dated Dec. 18, 2020.
Response to Office Action for U.S. Appl. No. 16/680,054 dated Dec. 11, 2020.
Response to Office Action for U.S. Appl. No. 16/698,422 dated Dec. 11, 2020.
Office Action in CA 2,842,672 dated Jan. 21, 2021.
Sorci et al., "Inflammation and oxidative stress in vertebrate host-parasite systems," Phil. Tans. R. Soc. B (2009) 364, pp. 71-83.
English Translation of Notice of Reexamination in CN 201280051863 dated Dec. 24, 2020.
Office Action for U.S. Appl. No. 16/680,054 dated Mar. 10, 2021.
Office Action for U.S. Appl. No. 16/698,422 dated Mar. 17, 2021.
Amendment for U.S. Appl. No. 13/335,341 date Apr. 5, 2021.
Amendment for U.S. Appl. No. 13/334,933 dated Jul. 22, 2016.
Office Action for U.S. Appl. No. 13/335,341 dated Jun. 1, 2016.
Office Action for U.S. Appl. No. 14/238,822 dated Jun. 8, 2016.
Response for U.S. Appl. No. 14/238,822 dated Aug. 8, 2016.
Office Action for U.S. Appl. No. 14/238,822 dated Sep. 6, 2016.
Office Action in CA 2,846,603 dated Jun. 7, 2016.
Second Office Action in CN 201280046188.2 dated Nov. 9, 2015.
Decision of Rejection in CN 201280046188.2 dated Jun. 8, 2016.
Third Office Action in CN 201280051863.00 dated Apr. 5, 2016.
Communication for EP Application No. 11811618.5 dated Jul. 18, 2016.
Communication for EP Application No. 12741201.3 dated Mar. 16, 2016.
Exam Report for ID Application No. P00201400846 dated Jun. 26, 2016.
Exam Report for ID Application No. P00 2014 01703 dated Jul. 8, 2016.
Second Office Action in MX/a/2013/007675 dated Jun. 14, 2016.
Further Examination Report in NZ 620,311 dated May 24, 2016.
Final Examination Report in SG 2013050067 dated Feb. 19, 2016.
Final Examination Report in SG 201305083-6 dated May 19, 2016.
Written Opinion in SG 2014004907 dated Apr. 12, 2016.
Search Report in TW Application No. 101126368 dated May 2, 2016.
Decision in TW Application No. 100150004 dated Jan. 28, 2016.

(56) References Cited

OTHER PUBLICATIONS

Kanamori et al. "Experience of long-term synbiotic therapy in seven short bowel patients with refractory enterocololitis," Journal of Pediatric Surgery, vol. 39, No. 11 (2004) pp. 1686-1692.
Leforestier et al., "Effects of galacto-oligosaccharide ingestion on the mucosa-associated mucins and sucrose activity in the small intestine of mice," Eur J. Nutr. (Dec. 2009), 48(8), pp. 457-464.
Miñana, "Oligosacaridos en la leche humana," Acta Pediatr Esp. (2007), 65(3), pp. 129-133.
Morrow et al., "Human-Milk Glycans that Inhibit Pathogen Binding Protect Breast-feeding Infants against Infectious Diarrhea," J. of Nutrition, American Society for Nutrition, v. 135, No. 5 (May 1, 2005), pp. 1304-1307.
English translation of Reexam Decision from Chinese Application No. 201280051863.0 dated May 27, 2021.
U.S. Appl. No. 61/428,863.
U.S. Appl. No. 61/428,865.
Amendment for U.S. Appl. No. 13/335,341 dated Oct. 29, 2021.
Response to Office Action for U.S. Appl. No. 15/791,052 dated Nov. 11, 2021.
Notice of Allowance for U.S. Appl. No. 15/791,052 dated Dec. 8, 2021.
Office Action for U.S. Appl. No. 16/698,422 dated Dec. 27, 2021.
Summons to Attend Oral Proceedings for EP Application No. 11813500.3 dated Sep. 30, 2021.
Yasunari et al., Current Pharmaceutical Biotechnology, 2006, 7, 73-80.
Amendment for U.S. Appl. No. 13/335,341 dated Mar. 5, 2018.
Office Action for U.S. Appl. No. 15/401,488 dated Apr. 4, 2018.
Decision on Rejection in ON 201280051863.0 dated Feb. 14, 2018.
Substantive Examination Report in PH 1-2014-500185 dated Jan. 11, 2018.
Substantive Examination Report in PH 1-2013-501291 dated Jan. 26, 2018.
Substantive Examination Report in PH 1-2014-500394 dated Jan. 26, 2018.
Office Action in TW Application No. 101126368 dated Mar. 1, 2018.
Xiao-Ming "Nutritional Management of Newborn Infants: Practical Guidelines," World J. Gastroenterol, 14(40), 6133-6139, Oct. 28, 2008.
Office Action for U.S. Appl. No. 13/335,341 dated Jun. 29, 2021.
Response to Office Action for U.S. Appl. No. 16/680,054 dated Jun. 10, 2021.
Notice of Allowance for U.S. Appl. No. 16/680,054 dated Jul. 19, 2021.
Response to Office Action for U.S. Appl. No. 16/698,422 dated Jun. 17, 2021.
Office Action from Chinese Application No. 201711012480.3 dated May 18, 2021.
Office Action for U.S. Appl. No. 15/791,052 dated Aug. 11, 2021.
Ledo, et al., "Human milk enhances antioxidant defenses against hydroxyl radical aggression in preterm infants", Am J Clini. Nutr., 2009, pp. 210-215.

* cited by examiner

GALACTOOLIGOSACCHARIDES FOR PREVENTING INJURY AND/OR PROMOTING HEALING OF THE GASTROINTESTINAL TRACT

CROSS REFERENCE TO RELATED APPLICATIONS

This application is the U.S. national stage entry of PCT/US12/47307, with an international filing date of 19 Jul. 2012, which is herein incorporated by reference in its entirety and which claims priority to and any other benefit of U.S. Provisional Application Ser. No. 61/510,632, with a filing date of 22 Jul. 2011, which is herein incorporated by reference in its entirety.

FIELD OF THE DISCLOSURE

The present disclosure relates to the use of galactooligosaccharides for preventing injury to the gastrointestinal tract and/or enhancing the healing of an injured gastrointestinal tract in an individual. More particularly, the present disclosure relates to human milk fortifiers, preterm and term infant formulas, pediatric formulas, follow on formulas, and adult nutritionals comprising galactooligosaccharides that can enhance the expression of various mucin-associated proteins, thereby improving an individual's gastrointestinal prevention and repair function.

BACKGROUND OF THE DISCLOSURE

Individuals undergoing various therapies or having various diseases and/or conditions are generally more susceptible to intestinal mucosa (gastrointestinal) injury than are healthy individuals. The expression of mucin-associated proteins, or secretory proteins, is an integral part of an individual's natural ability to prevent and/or repair intestinal injuries. Specifically, the expression of these mucin-associated proteins aids in the healing of intestinal mucosa injuries and in the prevention of further injuries by protecting the mucosa from insults, stabilizing the mucus layer, reducing inflammation of the mucus layer, and promoting the healing of the epithelial tissue.

Not all individuals, however, have an adequate expression of mucin-associated proteins to affect prevention and needed intestinal repair, which may result in an increased risk of translocation, sepsis, and possibly death. Further, there are currently no commercially available nutritional compositions that contain mucin-associated proteins, such as trefoil factor 3 (TFF3), or known methods of increasing the expression of mucin-associated proteins through the administration of an additional component to aid individuals having inadequate natural intestinal repair functions.

As such, it would be desirable to provide nutritional compositions that can produce nutritional benefits such as aiding in the prevention and healing of intestinal mucosal injuries by enhancing the expression of mucin-associated proteins. It would additionally be beneficial if the nutritional compositions could also improve the barrier function and reduce the inflammation of the injured gastrointestinal tract.

SUMMARY OF THE DISCLOSURE

The present disclosure is directed to the use of nutritional compositions, including human milk fortifiers, preterm and term infant formulas, pediatric formulas, follow on formulas and adult formulas including galactooligosaccharides alone or in combination with other components such as other prebiotic oligosaccharides and/or probiotics, for preventing injury to the gastrointestinal tract and/or enhancing the healing of the gastrointestinal tract of an infant, toddler, child, or adult. More particularly, the nutritional compositions can improve gastrointestinal healing through enhancing the expression of various mucin-associated proteins, which can stabilize the mucus layer, reduce inflammation, and promote healing of epithelial tissue.

One embodiment is directed to a method of enhancing healing of the gastrointestinal tract of an individual. The method comprises identifying an individual having an injured gastrointestinal tract and administering to the individual a nutritional composition comprising a galactooligosaccharide.

Another embodiment is directed to a method of reducing the incidence of intestinal mucosa injury. The method comprises identifying an individual susceptible to an intestinal mucosa injury and administering to the individual a nutritional composition comprising a galactooligosaccharide.

Another embodiment is directed to a method of improving the barrier function in the gastrointestinal tract of an individual. The method comprises identifying an individual in need of an increased barrier function of the gastrointestinal tract and administering to the individual a nutritional composition comprising a galactooligosaccharide.

Another embodiment is directed to a method of reducing the incidence of inflammation of the gastrointestinal tract of an individual. The method comprises identifying an individual susceptible to inflammation of the gastrointestinal tract and administering to the individual a nutritional composition comprising a galactooligosaccharide.

It has now been discovered that galactooligosaccharides can enhance the expression of various mucin-associated proteins, such as TFF3, MUC-2, and RELMb, which are an integral part of the intestinal repair system. Specifically, it has been found that enhancing the expression of these mucin-associated proteins through the administration of a composition containing galactooligosaccharides, aids in cell healing, resolution of inflammation, and promotion of barrier function.

DETAILED DESCRIPTION OF THE DISCLOSURE

Figure 1A:
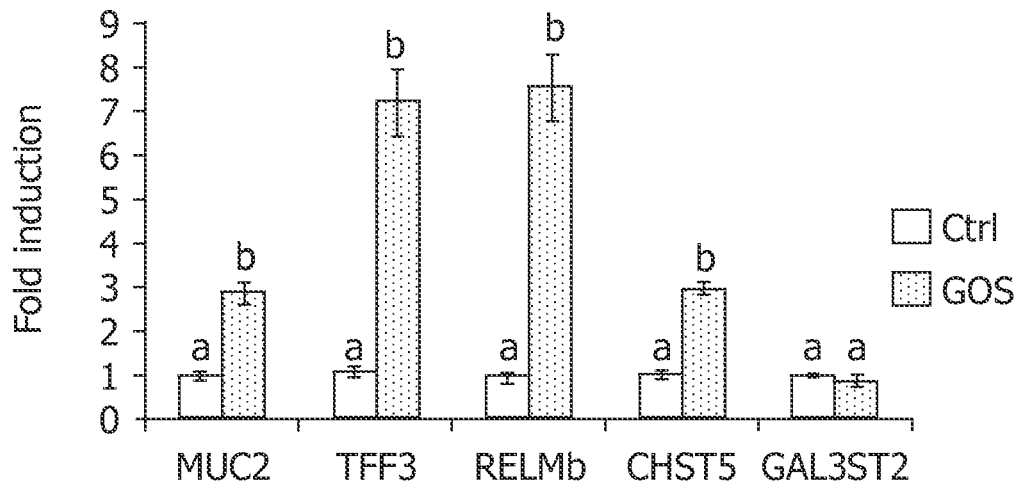
FIGS. 1A-1C are charts depicting the effect of galactooligosaccharides on the expression of several genes involved in the healing response of the gastrointestinal tract as measured in Example 20.

The nutritional compositions and methods described herein utilize galactooligosaccharides (GOS) alone or in combination with one or more additional components for preventing injury to the gastrointestinal tract and/or enhancing the healing of the gastrointestinal tract. These and other essential features of the nutritional compositions and methods, as well as some of the many optional variations and additions, are described in detail hereafter.

The term "retort packaging" and "retort sterilizing" are used interchangeably herein, and unless otherwise specified, refer to the common practice of filling a container, most typically a metal can or other similar package, with a nutritional liquid and then subjecting the liquid-filled package to the necessary heat sterilization step, to form a sterilized, retort packaged, nutritional liquid product.

The term "aseptic packaging" as used herein, unless otherwise specified, refers to the manufacture of a packaged product without reliance upon the above-described retort packaging step, wherein the nutritional liquid and package are sterilized separately prior to filling, and then are combined under sterilized or aseptic processing conditions to form a sterilized, aseptically packaged, nutritional liquid product.

The terms "fat" and "oil" as used herein, unless otherwise specified, are used interchangeably to refer to lipid materials derived or processed from plants or animals. These terms also include synthetic lipid materials so long as such synthetic materials are suitable for oral administration to humans.

The term "human milk oligosaccharide" or "HMO", unless otherwise specified, refers generally to a number of complex carbohydrates found in human breast milk that can be in acidic or neutral form, and to precursors thereof. Exemplary non-limiting human milk oligosaccharides include 3'-sialyllactose, 6'-sialyllactose, 3'-fucosyllactose, 2'-fucosyllactose, and lacto-N-neo-tetraose. An exemplary human milk oligosaccharide precursor includes sialic acid.

The term "shelf stable" as used herein, unless otherwise specified, refers to a nutritional product that remains commercially stable after being packaged and then stored at 18-24° C. for at least 3 months, including from about 6 months to about 24 months, and also including from about 12 months to about 18 months.

The terms "nutritional formulation" or "nutritional composition" as used herein, are used interchangeably and, unless otherwise specified, refer to synthetic formulas including nutritional liquids, nutritional powders, nutritional supplements, and any other nutritional food product as known in the art. The nutritional powders may be reconstituted to form a nutritional liquid, all of which comprise one or more of fat, protein and carbohydrate and are suitable for oral consumption by a human.

The term "nutritional liquid" as used herein, unless otherwise specified, refers to nutritional compositions in ready-to-drink liquid form, concentrated form, and nutritional liquids made by reconstituting the nutritional powders described herein prior to use.

The term "nutritional powder" as used herein, unless otherwise specified, refers to nutritional compositions in flowable or scoopable form that can be reconstituted with water or another aqueous liquid prior to consumption and includes both spraydried and drymixed/dryblended powders.

The term "infant" as used herein, unless otherwise specified, refers to a person 12 months or younger. The term "preterm infant" as used herein, refers to a person born prior to 36 weeks of gestation.

The term "toddler" as used herein, unless otherwise specified, refers to a person greater than one year of age up to three years of age.

The term "child" as used herein, unless otherwise specified, refers to a person greater than three years of age up to twelve years of age.

The term "newborn" as used herein, unless otherwise specified, refers to a person from birth up to four weeks of age.

The terms "infant formula" or "synthetic infant formula" as used herein, unless otherwise specified, are used interchangeably and refer to liquid and solid human milk replacements or substitutes that are suitable for consumption by an infant. The synthetic formulas include components that are of semi-purified or purified origin. As used herein, unless otherwise specified, the terms "semi-purified" or "purified" refer to a material that has been prepared by purification of a natural material or by synthesis. The terms "infant formula" or "synthetic infant formula" do not include human breast milk.

The term "preterm infant formula" as used herein, unless otherwise specified, refers to liquid and solid nutritional products suitable for consumption by a preterm infant.

The term "human milk fortifier" as used herein, unless otherwise specified, refers to liquid and solid nutritional products suitable for mixing with breast milk or preterm infant formula or infant formula for consumption by a preterm or term infant.

The terms "susceptible" and "at risk" as used herein, unless otherwise specified, mean having little resistance to a certain condition or disease, including being genetically predisposed, having a family history of, and/or having symptoms of the condition or disease.

All percentages, parts and ratios as used herein, are by weight of the total composition, unless otherwise specified. All such weights, as they pertain to listed ingredients, are based on the active level and, therefore, do not include solvents or by-products that may be included in commercially available materials, unless otherwise specified.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from κ to 6, from 1 to 9, from 3.6 to 4.6, from 3.5 to 9.9, and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The nutritional compositions and methods may comprise, consist of, or consist essentially of the essential elements of the compositions and methods as described herein, as well as any additional or optional element described herein or otherwise useful in nutritional composition applications.

Product Form

The nutritional compositions of the present disclosure including the GOS may be formulated and administered in any known or otherwise suitable oral product form. Any solid, liquid, or powder product form, including combinations or variations thereof, are suitable for use herein, provided that such forms allow for safe and effective oral delivery to the individual of the essential ingredients and any optional ingredients, as also defined herein.

The nutritional compositions of the present disclosure are preferably formulated as dietary product forms, which are defined herein as those embodiments comprising the essential ingredients of the present disclosure in a product form that then contains at least one of fat, protein, and carbohydrate, and preferably also contains vitamins, minerals, or combinations thereof. The nutritional compositions will comprise GOS, desirably in combination with at least one of protein, fat, vitamins, and minerals, to produce a nutritional combination.

The nutritional composition may be formulated with sufficient kinds and amounts of nutrients to provide a sole, primary, or supplemental source of nutrition, or to provide a specialized nutritional composition for use in individuals afflicted with specific diseases, disorders, or conditions or with a targeted nutritional benefit as described below.

Specific non-limiting examples of product forms suitable for use with the GOS-containing compositions as disclosed herein include, for example, liquid and powdered dietary supplements, liquid and powdered human milk fortifiers, liquid and powdered preterm infant formulas, liquid and powdered infant formulas, liquid and powdered elemental and semi-elemental formulas, liquid and powdered pediatric formulas, liquid and powdered toddler formulas, liquid and powdered follow-on formulas, liquid, powdered and solid adult nutritional formulas suitable for use with individuals suffering from enteric infection, inflammatory bowel disease, colitis, bowel obstruction, chronic stress, and other gastrointestinal diseases, conditions, and/or disorders or undergoing antibiotic therapy, radiation therapy, other chemotherapy, surgery, or other treatments or therapies.

Nutritional Liquids

Nutritional liquids include both concentrated and ready-to-feed nutritional liquids. These nutritional liquids are most typically formulated as suspensions or emulsions, although other liquid forms are within the scope of the present disclosure.

Nutritional emulsions suitable for use may be aqueous emulsions comprising proteins, fats, and carbohydrates. These emulsions are generally flowable or drinkable liquids at from about 1° C. to about 25° C. and are typically in the form of oil-in-water, water-in-oil, or complex aqueous emulsions, although such emulsions are most typically in the form of oil-in-water emulsions having a continuous aqueous phase and a discontinuous oil phase.

The nutritional emulsions may be and typically are shelf stable. The nutritional emulsions typically contain up to about 95% by weight of water, including from about 50% to about 95%, also including from about 60% to about 90%, and also including from about 70% to about 85%, by weight of water. The nutritional emulsions may have a variety of product densities, but most typically have a density greater than about 1.03 g/mL, including greater than about 1.04 g/mL, including greater than about 1.055 g/mL, including from about 1.06 g/ml to about 1.12 g/mL, and also including from about 1.085 g/mL to about 1.10 g/mL.

The nutritional emulsions may have a caloric density tailored to the nutritional needs of the ultimate user, although in most instances the emulsions comprise generally at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in preterm or low birth weight infants, and the 20-21 kcal/fl oz (675-680 to 700 kcal/liter) formulas are more often used in term infants. In some embodiments, the emulsion may have a caloric density of from about 50-100 kcal/liter to about 2000 kcal/liter, including from about 150 kcal/liter to about 500 kcal/liter. In some specific embodiments, the emulsion may have a caloric density of 25, or 50, or 75, or 100 kcal/liter.

The nutritional emulsion may have a pH ranging from about 3.5 to about 8, but are most advantageously in a range of from about 4.5 to about 7.5, including from about 5.5 to about 7.3, including from about 6.2 to about 7.2.

Although the serving size for the nutritional emulsion can vary depending upon a number of variables, a typical serving size is generally at least about 1 mL, or even at least about 2 mL, or even at least about 5 mL, or even at least about 10 mL, or even at least about 25 mL, including ranges from about 2 mL to about 500 mL, including from about 4 mL to about 340 mL, and including from about 10 mL to about 240 mL.

Nutritional Solids

The nutritional solids may be in any solid form, but are typically in the form of flowable or substantially flowable particulate compositions, or at least particulate compositions. Particularly suitable nutritional solid product forms include spray dried, agglomerated and/or dryblended powder compositions. The compositions can easily be scooped and measured with a spoon or similar other device, and can easily be reconstituted by the intended user with a suitable aqueous liquid, typically water, to form a nutritional composition for immediate oral or enteral use. In this context, "immediate" use generally means within about 48 hours, most typically within about 24 hours, preferably right after reconstitution.

The nutritional powders may be reconstituted with water prior to use to a caloric density tailored to the nutritional needs of the ultimate user, although in most instances the powders are reconstituted with water to form compositions comprising at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in preterm or low birth weight infants, and the 20-21 kcal/fl oz (675-680 to 700 kcal/liter) formulas are more often used in term infants. In some embodiments, the reconstituted powder may have a caloric density of from about 50-100 kcal/liter to about 2000 kcal/liter, including from about 150 kcal/liter to about 500 kcal/liter. In some specific embodiments, the emulsion may have a caloric density of 25, or 50, or 75, or 100 kcal/liter.

Galactooligosaccharides

The nutritional compositions of the present disclosure include galactose-containing oligosaccharides, commonly referred to as galactooligosaccharides (GOS). GOS are indigestible oligosaccharides containing one or more galactose molecule and one molecule of glucose connected through β(1,4) and/or β(1,6) glycosidic bonds. The GOS used in the compositions of the present disclosure may be selected from β-galactooligosaccharides, α-galactooligosaccharides, and combinations thereof. In some embodiments, the GOS may be trans-galactooligosaccharides (T-GOS), which are a mixture of oligosaccharides consisting of D-glucose and D-galactose alone, or in combination with one or more other forms of GOS. T-GOS are produced from D-lactose via the action of the enzyme beta-galactosidase obtained from *Aspergillus oryzae*. T-GOS are resistant to digestion in the upper gastrointestinal tract and stimulate the growth of bifidobacteria in the large intestine.

The GOS may be generally represented by the formula: [galactose]n-glucose, wherein n is an integer between 1 and 20, and preferably is selected from 2, 3, 4, 5, 6, 7, 8, 9, or 10. The term "galactooligosaccharide" or "GOS" may also refer to a mixture of galactooligosaccharides having different chain lengths; that is, long chain lengths and/or short chain lengths. Galactooligosaccharides are commercially available as, for example, Vivinal® GOS (75% total solids, 60% of total solids GOS; Friesland) and GOS (Clasado).

The GOS is present in the nutritional compositions in a total amount of from about 5 kg to about 160 kg per 1000 kg of nutritional composition, including from about 8 kg to about 160 kg per 1000 kg of nutritional composition, including from about 8 kg to about 80 kg per 1000 kg, including from about 8 kg to about 64 kg per 1000 kg, and including from about 164 kg to about 818 kg per 18,000 pounds of nutritional composition. In one embodiment, the nutritional composition is a human milk fortifier that provides GOS to a 1 kg preterm infant in an amount of from about 0.11 g to about 0.55 g of GOS per day.

Additional Prebiotic Oligosaccharides

The nutritional compositions of the present disclosure may, in addition to the GOS described above, comprise an additional source or sources of prebiotic oligosaccharides. Suitable additional sources of prebiotic oligosaccharides for use in the nutritional compositions include any prebiotic oligosaccharide that is suitable for use in a nutritional composition and is compatible with the essential elements and features of such compositions. In some embodiments, the nutritional composition includes a combination of GOS and one or more additional prebiotic oligosaccharide such that the composition provides a synergistic benefit to the end user, such as a synergistic benefit in improving the barrier function of the gastrointestinal tract.

Non-limiting examples of suitable additional prebiotic oligosaccharides for use in the nutritional compositions described herein include prebiotic oligosaccharides that have a degree of polymerization (DP) of at least 2 monose units, which are not or only partially digested in the intestine by the action of acids or digestive enzymes present in the human upper digestive tract (small intestine and stomach), but which are fermentable by the human intestinal flora. The term "monose units" refers to units having a closed ring structure, preferably hexose, e.g., the pyranose or furanose forms. Particularly preferred oligosaccharides for use in combination with the GOS in the nutritional compositions of the present disclosure include fructooligosaccharides (FOS), short chain fructooligosaccharides, inulin, polydextrose (PDX), pectin hydrolysate, and gum fiber.

Probiotics

The nutritional compositions of the present disclosure may further comprise one or more probiotics in addition to the GOS.

Non-limiting examples of suitable probiotic strains for use in the nutritional compositions including GOS herein include the genus *Lactobacillus* including *L. acidophilus*, *L. amylovorus*, *L. brevis*, *L. bulgaricus*, *L. casei* spp. *casei*, *L. casei* spp. *rhamnosus*, *L. crispatus*, *L. delbrueckii* ssp. *lactis*, *L. fermentum*, *L. helveticus*, *L. johnsonii*, *L. paracasei*, *L. pentosus*, *L. plantarum*, *L. reuteri*, and *L. sake*; the genus *Bifidobacterium* including: *B. animalis*, *B. bifidum*, *B. breve*, *B. infantis*, *B. lactis* and *B. longum*; the genus *Pediococcus* including: *P. acidilactici*; the genus *Propionibacterium* including: *P. acidipropionici*, *P. freudenreichii*, *P. jensenii*, and *P. theonii*; and the genus *Streptococcus* including: *S. cremoris*, *S. lactis*, and *S. thermophilus*. Particularly preferred probiotics include *B. lactis* and *L. acidophilus*.

The probiotics may be present in the nutritional compositions in a total amount of at least about $10^4$ CFU/g composition, including from about $10^4$ CFU/g composition to about $10^{11}$ CFU/g composition, and including from about $10^5$ CFU/g composition to about $10^{10}$ CFU/g composition.

Macronutrients

The nutritional compositions including the GOS may be formulated to include at least one of protein, fat, and carbohydrate. In many embodiments, the nutritional compositions will include the GOS in combination with protein, carbohydrate and fat.

Although total concentrations or amounts of the fat, protein, and carbohydrates may vary depending upon the product type (i.e., human milk fortifier, preterm infant formula, infant formula, toddler formula, pediatric formula, follow-on formula, adult nutritional, etc.), product form (i.e., nutritional solid, powder, ready-to-feed liquid, or concentrated liquid), and targeted dietary needs of the intended user, such concentrations or amounts most typically fall within one of the following embodied ranges, inclusive of any other essential fat, protein, and/or carbohydrate ingredients as described herein.

For the liquid preterm and term infant formulas, carbohydrate concentrations (including both GOS and any other carbohydrate/oligosaccharide sources) most typically range from about 5% to about 40%, including from about 7% to about 30%, including from about 10% to about 25%, by weight of the preterm or term infant formula; fat concentrations most typically range from about 1% to about 30%, including from about 2% to about 15%, and also including from about 3% to about 10%, by weight of the preterm or term infant formula; and protein concentrations most typically range from about 0.5% to about 30%, including from about 1% to about 15%, and also including from about 2% to about 10%, by weight of the preterm or term infant formula.

For the liquid human milk fortifiers, carbohydrate concentrations (including both GOS and any other carbohydrate/oligosaccharide sources) most typically range from about 10% to about 75%, including from about 10% to about 50%, including from about 20% to about 40%, by weight of the human milk fortifier; fat concentrations most typically range from about 10% to about 40%, including from about 15% to about 37%, and also including from about 18% to about 30%, by weight of the human milk fortifier; and protein concentrations most typically range from about 5% to about 40%, including from about 10% to about 30%, and also including from about 15% to about 25%, by weight of the human milk fortifier.

For the adult nutritional liquids, carbohydrate concentrations (including both GOS and any other carbohydrate/oligosaccharide sources) most typically range from about 5% to about 40%, including from about 7% to about 30%, including from about 10% to about 25%, by weight of the adult nutritional; fat concentrations most typically range from about 2% to about 30%, including from about 3% to about 15%, and also including from about 5% to about 10%, by weight of the adult nutritional; and protein concentrations most typically range from about 0.5% to about 30%, including from about 1% to about 15%, and also including from about 2% to about 10%, by weight of the adult nutritional.

The amount of carbohydrates, fats, and/or proteins in any of the liquid nutritional compositions described herein may also be characterized in addition to, or in the alternative, as a percentage of total calories in the liquid nutritional composition as set forth in the following table. These macronutrients for liquid nutritional compositions of the present disclosure are most typically formulated within any of the caloric ranges (embodiments A-F) described in the following table (each numerical value is preceded by the term "about").

| Nutrient % Total Cal. | Embodiment A | Embodiment B | Embodiment C |
|---|---|---|---|
| Carbohydrate | 0-98 | 2-96 | 10-75 |
| Protein | 0-98 | 2-96 | 5-70 |
| Fat | 0-98 | 2-96 | 20-85 |
|  | Embodiment D | Embodiment E | Embodiment F |
| Carbohydrate | 30-50 | 25-50 | 25-50 |
| Protein | 15-35 | 10-30 | 5-30 |
| Fat | 35-55 | 1-20 | 2-20 |

In one specific example, liquid infant formulas (both ready-to-feed and concentrated liquids) include those embodiments in which the protein component may comprise from about 7.5% to about 25% of the caloric content of the formula; the carbohydrate component (including both GOS and any other carbohydrate/oligosaccharide sources) may comprise from about 35% to about 50% of the total caloric content of the infant formula; and the fat component may comprise from about 30% to about 60% of the total caloric content of the infant formula. These ranges are provided as examples only, and are not intended to be limiting. Additional suitable ranges are noted in the following table (each numerical value is preceded by the term "about").

| Nutrient % Total Cal. | Embodiment G | Embodiment H | Embodiment I |
|---|---|---|---|
| Carbohydrates: | 20-85 | 30-60 | 35-55 |
| Fat: | 5-70 | 20-60 | 25-50 |
| Protein: | 2-75 | 5-50 | 7-40 |

When the nutritional composition is a powdered preterm or term infant formula, the protein component is present in an amount of from about 5% to about 35%, including from about 8% to about 12%, and including from about 10% to about 12% by weight of the preterm or term infant formula; the fat component is present in an amount of from about 10% to about 35%, including from about 25% to about 30%, and including from about 26% to about 28% by weight of the preterm or term infant formula; and the carbohydrate component (including both GOS and any other carbohydrate/oligosaccharide sources) is present in an amount of from about 30% to about 85%, including from about 45% to about 60%, including from about 50% to about 55% by weight of the preterm or term infant formula.

For powdered human milk fortifiers, the protein component is present in an amount of from about 1% to about 55%, including from about 10% to about 50%, and including from about 10% to about 30% by weight of the human milk fortifier; the fat component is present in an amount of from about 1% to about 30%, including from about 1% to about 25%, and including from about 1% to about 20% by weight of the human milk fortifier; and the carbohydrate component (including both GOS and any other carbohydrate/oligosaccharide sources) is present in an amount of from about 15% to about 75%, including from about 15% to about 60%, including from about 20% to about 50% by weight of the human milk fortifier.

For powdered adult nutritionals, the protein component is present in an amount of from about 10% to about 90%, including from about 30% to about 80%, and including from about 40% to about 75% by weight of the adult nutritional; the fat component is present in an amount of from about 0.5% to about 20%, including from about 1% to about 10%, and including from about 2% to about 5% by weight of the adult nutritional; and the carbohydrate component (including both GOS and any other carbohydrate/oligosaccharide sources) is present in an amount of from about 5% to about 40%, including from about 7% to about 30%, including from about 10% to about 25% by weight of the adult nutritional.

The total amount or concentration of fat, carbohydrate, and protein, in the powdered nutritional compositions of the present disclosure can vary considerably depending upon the selected composition and dietary or medical needs of the intended user. Additional suitable examples of macronutrient concentrations are set forth below. In this context, the total amount or concentration refers to all fat, carbohydrate, and protein sources in the powdered composition. For powdered nutritional compositions, such total amounts or concentrations are most typically and preferably formulated within any of the embodied ranges described in the following table (each numerical value is preceded by the term "about").

| Nutrient % Total Cal. | Embodiment J | Embodiment K | Embodiment L |
|---|---|---|---|
| Carbohydrate | 1-85 | 30-60 | 35-55 |
| Fat | 5-70 | 20-60 | 25-50 |
| Protein | 2-75 | 5-50 | 7-40 |

Fat

The nutritional compositions of the present disclosure may optionally comprise any source or sources of fat. Suitable sources of fat for use herein include any fat or fat source that is suitable for use in an oral nutritional composition and is compatible with the essential elements and features of such composition. For example, in one specific embodiment, the fat is derived from long chain polyunsaturated fatty acids (LCPUFAs).

Exemplary LCPUFAs for use in the nutritional compositions include, for example, ω-3 LCPUFAs and ω-6 LCPUFAs. Specific LCPUFAs include docosahexaenoic acid (DHA), eicosapentaenoic acid (EPA), arachidonic acid (ARA), linoleic acid, linolenic acid (alpha linolenic acid) and gamma-linolenic acid derived from oil sources such as plant oils, marine plankton, fungal oils, and fish oils. In one particular embodiment, the LCPUFAs are derived from fish oils such as menhaden, salmon, anchovy, cod, halibut, tuna, or herring oil. Particularly preferred LCPUFAs for use in the nutritional compositions with the HMOs include DHA, ARA, EPA, and combinations thereof.

In order to reduce potential side effects of high dosages of LCPUFAs in the nutritional compositions, the content of LCPUFAs preferably does not exceed 3% by weight of the total fat content, including below 2% by weight of the total fat content, and including below 1% by weight of the total fat content in the nutritional composition.

The LCPUFA may be provided as free fatty acids, in triglyceride form, in diglyceride form, in monoglyceride form, in phospholipid form, or as a mixture of one or more of the above, preferably in triglyceride form. In another specific embodiment, the fat is derived from short chain fatty acids.

Additional non-limiting examples of suitable fats or sources thereof for use in the nutritional compositions described herein include coconut oil, fractionated coconut oil, soybean oil, corn oil, olive oil, safflower oil, high oleic safflower oil, oleic acids (EMERSOL 6313 OLEIC ACID, Cognis Oleochemicals, Malaysia), MCT oil (medium chain triglycerides), sunflower oil, high oleic sunflower oil, palm and palm kernel oils, palm olein, canola oil, marine oils, fish oils, fungal oils, algae oils, cottonseed oils, and combinations thereof.

Protein

The nutritional compositions of the present disclosure may optionally further comprise protein. Any protein source that is suitable for use in oral nutritional compositions and is compatible with the essential elements and features of such compositions is suitable for use in the nutritional compositions.

Non-limiting examples of suitable proteins or sources thereof for use in the nutritional compositions include hydrolyzed, partially hydrolyzed or non-hydrolyzed proteins or protein sources, which may be derived from any known or otherwise suitable source such as milk (e.g., casein, whey), animal (e.g., meat, fish), cereal (e.g., rice, corn), vegetable (e.g., soy) or combinations thereof. Non-limiting examples of such proteins include milk protein isolates, milk protein concentrates as described herein, casein protein isolates, extensively hydrolyzed casein, whey protein, sodium or calcium caseinates, whole cow milk, partially or completely defatted milk, soy protein isolates, soy protein concentrates, and so forth. In one specific embodiment, the nutritional compositions include a protein source derived from milk proteins of human and/or bovine origin.

In one embodiment, the protein source is a hydrolyzed protein hydrolysate. In this context, the terms "hydrolyzed protein" or "protein hydrolysates" are used interchangeably herein and include extensively hydrolyzed proteins, wherein the degree of hydrolysis is most often at least about 20%, including from about 20% to about 80%, and also including from about 30% to about 80%, even more preferably from about 40% to about 60%. The degree of hydrolysis is the extent to which peptide bonds are broken by a hydrolysis method. The degree of protein hydrolysis for purposes of characterizing the extensively hydrolyzed protein component of these embodiments is easily determined by one of ordinary skill in the formulation arts by quantifying the amino nitrogen to total nitrogen ratio (AN/TN) of the protein component of the selected liquid formulation. The amino nitrogen component is quantified by USP titration methods for determining amino nitrogen content, while the total nitrogen component is determined by the Tecator Kjeldahl method, all of which are well known methods to one of ordinary skill in the analytical chemistry art.

Suitable hydrolyzed proteins may include soy protein hydrolysate, casein protein hydrolysate, whey protein hydrolysate, rice protein hydrolysate, potato protein hydrolysate, fish protein hydrolysate, egg albumen hydrolysate, gelatin protein hydrolysate, combinations of animal and vegetable protein hydrolysates, and combinations thereof. Particularly preferred protein hydrolysates include whey protein hydrolysate and hydrolyzed sodium caseinate.

When used in the nutritional compositions, the protein source may include at least about 20% (by weight total protein) protein hydrolysate, including from about 30% to 100% (by weight total protein) protein hydrolysate, and including from about 40% to about 80% (by weight total protein) protein hydrolysate, and including about 50% (by weight total protein) protein hydrolysate. In one particular embodiment, the nutritional composition includes 100% (by weight total protein) protein hydrolysate.

Carbohydrate

In addition to the GOS, the nutritional compositions of the present disclosure may further optionally comprise any other carbohydrates that are suitable for use in an oral nutritional composition and are compatible with the essential elements and features of such compositions.

Non-limiting examples of suitable carbohydrates or sources thereof for use in the nutritional compositions described herein may include maltodextrin, hydrolyzed or modified starch or cornstarch, glucose polymers, corn syrup, corn syrup solids, rice-derived carbohydrates, pea-derived carbohydrates, potato-derived carbohydrates, tapioca, sucrose, glucose, fructose, lactose, high fructose corn syrup, honey, sugar alcohols (e.g., maltitol, erythritol, sorbitol), artificial sweeteners (e.g., sucralose, acesulfame potassium, stevia) and combinations thereof. A particularly desirable carbohydrate is a low dextrose equivalent (DE) maltodextrin.

Other Optional Ingredients

The nutritional compositions of the present disclosure may further comprise other optional components that may modify the physical, chemical, aesthetic or processing characteristics of the compositions or serve as pharmaceutical or additional nutritional components when used in the targeted population. Many such optional ingredients are known or otherwise suitable for use in medical food or other nutritional products or pharmaceutical dosage forms and may also be used in the compositions herein, provided that such optional ingredients are safe for oral administration and are compatible with the essential and other ingredients in the selected product form.

Non-limiting examples of such optional ingredients include human milk oligosaccharides, preservatives, emulsifying agents, buffers, pharmaceutical actives, anti-inflammatory agents, additional nutrients as described herein, colorants, flavors, thickening agents and stabilizers, emulsifying agents, lubricants, and so forth.

The nutritional compositions may further comprise a sweetening agent, preferably including at least one sugar alcohol such as maltitol, erythritol, sorbitol, xylitol, mannitol, isolmalt, and lactitol, and also preferably including at least one artificial or high potency sweetener such as acesulfame K, aspartame, sucralose, saccharin, stevia, and tagatose. These sweetening agents, especially as a combination of a sugar alcohol and an artificial sweetener, are especially useful in formulating liquid beverage embodiments of the present disclosure having a desirable favor profile. These sweetener combinations are especially effective in masking undesirable flavors sometimes associated with the addition of vegetable proteins to a liquid beverage. Optional sugar alcohol concentrations in the nutritional composition may range from at least 0.01%, including from 0.1% to about 10%, and also including from about 1% to about 6%, by weight of the nutritional composition. Optional artificial sweetener concentrations may range from about 0.01%, including from about 0.05% to about 5%, also including from about 0.1% to about 1.0%, by weight of the nutritional composition.

A flowing agent or anti-caking agent may be included in the nutritional compositions as described herein to retard clumping or caking of the powder over time and to make a powder embodiment flow easily from its container. Any known flowing or anti-caking agents that are known or otherwise suitable for use in a nutritional powder or product form are suitable for use herein, non-limiting examples of which include tricalcium phosphate, silicates, and combinations thereof. The concentration of the flowing agent or anti-caking agent in the nutritional composition varies depending upon the product form, the other selected ingredients, the desired flow properties, and so forth, but most typically range from about 0.1% to about 4%, including from about 0.5% to about 2%, by weight of the nutritional composition.

A stabilizer may also be included in the nutritional compositions. Any stabilizer that is known or otherwise suitable for use in a nutritional composition is also suitable for use herein, some non-limiting examples of which include gums such as xanthan gum. The stabilizer may represent from about 0.1% to about 5.0%, including from about 0.5% to about 3%, including from about 0.7% to about 1.5%, by weight of the nutritional composition.

Additionally, the nutritional compositions may comprise one or more antioxidants to provide nutritional support, as well as to reduce oxidative stress. Any antioxidants suitable for oral administration may be included for use in the nutritional compositions of the present disclosure, including, for example, vitamin A, vitamin E, vitamin C, retinol, tocopherol, and carotenoids.

In one specific embodiment, the antioxidants for use in the nutritional compositions include carotenoids such as lutein, zeaxanthin, lycopene, beta-carotene, and combinations thereof, and particularly, combinations of the carotenoids lutein, lycopene, and beta-carotene. Nutritional compositions containing these combinations, as selected and defined herein, can be used to modulate inflammation and/or levels of C-reactive protein in preterm and term infants The nutritional compositions may further comprise any of a variety of other vitamins or related nutrients, non-limiting examples of which include vitamin D, vitamin K, thiamine, riboflavin, pyridoxine, vitamin $B_{12}$, niacin, folic acid, pantothenic acid, biotin, choline, inositol, salts and derivatives thereof, and combinations thereof.

The nutritional compositions may further comprise any of a variety of other additional minerals, non-limiting examples of which include calcium, phosphorus, magnesium, iron, zinc, manganese, copper, sodium, potassium, molybdenum, chromium, chloride, and combinations thereof.

The nutritional compositions of the present disclosure may additionally comprise nucleotides and/or nucleotide precursors selected from the group consisting of nucleoside, purine base, pyrimidine base, ribose and deoxyribose to further improve intestinal barrier integrity and/or maturation. The nucleotide may be in monophosphate, diphosphate, or triphosphate form. The nucleotide may be a ribonucleotide or a deoxyribonucleotide. The nucleotides may be monomeric, dimeric, or polymeric (including RNA and DNA). The nucleotide may be present in the nutritional composition as a free acid or in the form of a salt, preferably a monosodium salt.

Suitable nucleotides and/or nucleosides for use in the nutritional compositions include one or more of cytidine 5'-monophosphate, uridine 5'-monophosphate, adenosine 5'-monophosphate, guanosine 5'-1-monophosphate, and/or inosine 5'-monophosphate, more preferably cytidine 5'-monophosphate, uridine 5'-monophosphate, adenosine 5'-monophosphate, guanosine 5'-monophosphate, and inosine 5'-monophosphate.

Methods of Manufacture

The nutritional compositions of the present disclosure may be prepared by any known or otherwise effective manufacturing technique for preparing the selected product solid or liquid form. Many such techniques are known for any given product form such as nutritional liquids or powders and can easily be applied by one of ordinary skill in the art to the nutritional compositions described herein.

The nutritional compositions of the present disclosure can therefore be prepared by any of a variety of known or otherwise effective formulation or manufacturing methods. In one suitable manufacturing process, for example, at least three separate slurries are prepared, including a protein-in-fat (PIF) slurry, a carbohydrate-mineral (CHO-MIN) slurry, a protein-in-water (PIW) slurry. The PIF slurry is formed by heating and mixing the oil (e.g., canola oil, corn oil, etc.) and then adding an emulsifier (e.g., lecithin), fat soluble vitamins, and a portion of the total protein (e.g., milk protein concentrate, etc.) with continued heat and agitation. The CHO-MIN slurry is formed by adding with heated agitation to water: minerals (e.g., potassium citrate, dipotassium phosphate, sodium citrate, etc.), trace and ultra trace minerals (TM/UTM premix), thickening or suspending agents (e.g. avicel, gellan, carrageenan). The resulting CHO-MIN slurry is held for 10 minutes with continued heat and agitation before adding additional minerals (e.g., potassium chloride, magnesium carbonate, potassium iodide, etc.), and/or carbohydrates (e.g., GOS, HMOs, fructooligosaccharide, sucrose, corn syrup, etc.). The PIW slurry is then formed by mixing with heat and agitation the remaining protein, if any.

The resulting slurries are then blended together with heated agitation and the pH adjusted to 6.6-7.0, after which the composition is subjected to high-temperature short-time (HTST) processing during which the composition is heat treated, emulsified and homogenized, and then allowed to cool. Water soluble vitamins and ascorbic acid are added, the pH is adjusted to the desired range if necessary, flavors are added, and water is added to achieve the desired total solid level. The composition is then aseptically packaged to form an aseptically packaged nutritional emulsion. This emulsion can then be further diluted, heat-treated, and packaged to form a ready-to-feed or concentrated liquid, or it can be heat-treated and subsequently processed and packaged as a reconstitutable powder, e.g., spray dried, drymixed, agglomerated.

The nutritional solid, such as a spray dried nutritional powder or drymixed nutritional powder, may be prepared by any collection of known or otherwise effective techniques, suitable for making and formulating a nutritional powder.

For example, when the nutritional powder is a spray dried nutritional powder, the spray drying step may likewise include any spray drying technique that is known for or otherwise suitable for use in the production of nutritional powders. Many different spray drying methods and techniques are known for use in the nutrition field, all of which are suitable for use in the manufacture of the spray dried nutritional powders herein.

One method of preparing the spray dried nutritional powder comprises forming and homogenizing an aqueous slurry or liquid comprising predigested fat, and optionally protein, carbohydrate, and other sources of fat, and then spray drying the slurry or liquid to produce a spray dried nutritional powder. The method may further comprise the step of spray drying, drymixing, or otherwise adding additional nutritional ingredients, including any one or more of the ingredients described herein, to the spray dried nutritional powder.

Other suitable methods for making nutritional compositions are described, for example, in U.S. Pat. No. 6,365,218 (Borschel, et al.), U.S. Pat. No. 6,589,576 (Borschel, et al.), U.S. Pat. No. 6,306,908 (Carlson, et al.), U.S. Patent Application No. 20030118703 A1 (Nguyen, et al.), which descriptions are incorporated herein by reference to the extent that they are consistent herewith.

Methods of Use

The nutritional compositions as described herein and containing GOS can be used to prevent injury to the gastrointestinal tract and/or to enhance the healing of an injured gastrointestinal tract of preterm infants, infants, toddlers, children, and adults. Any of this group may actually have an injured gastrointestinal tract and thus benefit from the healing action of the GOS-containing nutritional composition, or may be at risk of or susceptible to sustaining injuries to the gastrointestinal tract and thus benefit from the preventative action of the GOS-containing nutritional composition.

The nutritional compositions as described herein comprise GOS, alone or in combination with one or more additional components, such as a probiotic as noted above, to provide a nutritional source for improving at least the intestinal repair/healing function of an individual. Specifically, the nutritional compositions can enhance the expression of mucin-associated proteins, such as trefoil factor 3 (TFF3), mucin 2 (MUC-2), and relm-beta (RELMb) to stabilize the mucus layer; promote healing of epithelial cells; improve barrier function; and reduce inflammation, each of which enhance the overall healing of the epithelial tissue and mucus layer of the stomach, small intestine, and large intestine.

More particularly, in some embodiments, the nutritional compositions may be administered to an individual who has sustained injury to the gastrointestinal tract or who is more susceptible to or at risk of injury to the gastrointestinal tract by having undergone various therapies, which may include, for example, antibiotic therapy, radiation therapy, chemotherapy, or surgery or by having various diseases or disorders, which may include, for example, enteric infection, inflammatory bowel diseases, colitis, bowel obstruction, and chronic stress.

The individual desirably consumes at least one serving of the GOS-containing nutritional composition daily, and in some embodiments, may consume two, three, or even more servings per day. Each serving is desirably administered as a single undivided dose, although the serving may also be divided into two or more partial or divided servings to be taken at two or more times during the day. The methods of the present disclosure include continuous day after day administration, as well as periodic or limited administration, although continuous day after day administration is generally desirable.

The nutritional composition may be administered to the individual orally or via tube feeding. The nutritional compositions of the present disclosure could also be given to preterm or term infants prior to the initiation of enteral feeding and/or concurrently with feeding. Furthermore, the nutritional composition may be given to infants, children, or adults prior to or concurrently with re-feeding after partial or total parenteral nutrition.

EXAMPLES

The following examples illustrate specific embodiments and/or features of the nutritional compositions and methods of the present disclosure. The examples are given solely for the purpose of illustration and are not to be construed as limitations of the present disclosure, as many variations thereof are possible without departing from the spirit and scope of the disclosure. All exemplified amounts are weight percentages based upon the total weight of the composition, unless otherwise specified.

The exemplified compositions are shelf stable nutritional compositions prepared in accordance with the manufacturing methods described herein, such that each exemplified composition, unless otherwise specified, includes an aseptically processed embodiment and a retort packaged embodiment.

The nutritional liquid embodiments are aqueous oil-in-water emulsions that are packaged in 240 mL plastic containers and remain physically stable for 12-18 months after composition/packaging at storage temperatures ranging from 1-25° C.

Examples 1-5

Examples 1-5 illustrate spray dried nutritional powders of the present disclosure, the ingredients of which are listed in the table below. All ingredient amounts are listed as kilogram per 1000 kilogram batch of product, unless otherwise specified.

| Ingredient | Ex. 1 | Ex. 2 | Ex. 3 | Ex. 4 | Ex. 5 |
| --- | --- | --- | --- | --- | --- |
| Corn syrup | 256.86 kg | 256.86 kg | 256.86 kg | 256.86 kg | 256.86 kg |
| Corn Maltodextrin | 216.25 kg | 216.25 kg | 216.25 kg | 216.25 kg | 216.25 kg |
| Sucrose | 177.95 kg | 177.95 kg | 177.95 kg | 177.95 kg | 177.95 kg |
| Corn oil | 155.40 kg | 155.40 kg | 155.40 kg | 155.40 kg | 155.40 kg |
| Casein | 132.97 kg | 132.97 kg | 132.97 kg | 132.97kg | 132.97 kg |
| Soy protein isolate | 29.84 kg | 29.84 kg | 29.84 kg | 29.84 kg | 29.84 kg |
| Calcium caseinate | 19.46 kg | 19.46 kg | 19.46 kg | 19.46 kg | 19.46 kg |
| 20% potassium citrate | 16.09 kg | 16.09 kg | 16.09 kg | 16.09 kg | 16.09 kg |
| Vanilla | 14.55 kg | 14.55 kg | 14.55 kg | 14.55 kg | 14.55 kg |
| 20% sodium hydroxide | 13.77 kg | 13.77 kg | 13.77 kg | 13.77 kg | 13.77 kg |

-continued

| Ingredient | Ex. 1 | Ex. 2 | Ex. 3 | Ex. 4 | Ex. 5 |
|---|---|---|---|---|---|
| Galactooligosaccharides | 8 kg | 40 kg | 80 kg | 120 kg | 160 kg |
| Potassium citrate | 7.54 kg | 7.54 kg | 7.54 kg | 7.54 kg | 7.54 kg |
| Magnesium chloride | 7.53 kg | 7.53 kg | 7.53 kg | 7.53 kg | 7.53 kg |
| Tricalcium phosphate | 6.23 kg | 6.23 kg | 6.23 kg | 6.23 kg | 6.23 kg |
| Sodium citrate | 5.66 kg | 5.66 kg | 5.66 kg | 5.66 kg | 5.66 kg |
| Potassium chloride | 3.79 kg | 3.79 kg | 3.79 kg | 3.79 kg | 3.79 kg |
| Soy lecithin | 3.44 kg | 3.44 kg | 3.44 kg | 3.44 kg | 3.44 kg |
| Ascorbic acid | 1.91 kg | 1.91 kg | 1.91 kg | 1.91 kg | 1.91 kg |
| Choline chloride | 1.64 kg | 1.64 kg | 1.64 kg | 1.64 kg | 1.64 kg |
| 45% KOH | 1.26 kg | 1.26 kg | 1.26 kg | 1.26 kg | 1.26 kg |
| Zinc sulfate | 0.1558 kg | 0.1558 kg | 0.1558 kg | 0.1558 kg | 0.1558 kg |
| Ferrous sulfate | 0.121700 kg | 0.121700 kg | 0.121700 kg | 0.121700 kg | 0.121700 kg |
| Manganese sulfate | 0.036900 kg | 0.036900 kg | 0.036900 kg | 0.036900 kg | 0.036900 kg |
| Cupric sulfate | 0.021100 kg | 0.021100 kg | 0.021100 kg | 0.021100 kg | 0.021100 kg |
| Chromium chloride | 0.001280 kg | 0.001280 kg | 0.001280 kg | 0.001280 kg | 0.001280 kg |
| Sodium molybdate | 0.001012 kg | 0.001012 kg | 0.001012 kg | 0.001012 kg | 0.001012 kg |
| Sodium selenate | 0.000434 kg | 0.000434 kg | 0.000434 kg | 0.000434 kg | 0.000434 kg |
| Niacinamide | 0.124200 kg | 0.124200 kg | 0.124200 kg | 0.124200 kg | 0.124200 kg |
| D-calcium pantothenate | 0.083000 kg | 0.083000 kg | 0.083000 kg | 0.083000 kg | 0.083000 kg |
| Thiamine chloride hydrochloride | 0.020510 kg | 0.020510 kg | 0.020510 kg | 0.020510 kg | 0.020510 kg |
| Pyridoxine hydrochloride | 0.019750 kg | 0.019750 kg | 0.019750 kg | 0.019750 kg | 0.019750 kg |
| Riboflavin | 0.016000 kg | 0.016000 kg | 0.016000 kg | 0.016000 kg | 0.016000 kg |
| Folic acid | 0.002783 kg | 0.002783 kg | 0.002783 kg | 0.002783 kg | 0.002783 kg |
| Biotin | 0.002419 kg | 0.002419 kg | 0.002419 kg | 0.002419 kg | 0.002419 kg |
| Cyanocobalamin | 0.000055 kg | 0.000055 kg | 0.000055 kg | 0.000055 kg | 0.000055 kg |
| dl-alpha-tocopheryl acetate | 0.129600 kg | 0.129600 kg | 0.129600 kg | 0.129600 kg | 0.129600 kg |
| Phylloquinone | 0.002162 kg | 0.002162 kg | 0.002162 kg | 0.002162 kg | 0.002162 kg |
| Vitamin D3 | 0.000028 kg | 0.000028 kg | 0.000028 kg | 0.000028 kg | 0.000028 kg |
| Vitamin A palmitate | 0.010373 kg | 0.010373 kg | 0.010373 kg | 0.010373 kg | 0.010373 kg |
| Potassium iodide | 0.000440 kg | 0.000440 kg | 0.000440 kg | 0.000440 kg | 0.000440 kg |

AN = as needed

Examples 6-10

Examples 6-10 illustrate spray dried nutritional powders of the present disclosure, the ingredients of which are listed in the table below. All ingredient amounts are listed as kilogram per 1000 kilogram batch of product, unless otherwise specified.

Examples 11-15

Examples 11-15 illustrate liquid emulsions of the present disclosure, the ingredients of which are listed in the table below. All ingredient amounts are listed as kilogram per 1000 kilogram batch of product, unless otherwise specified.

| Ingredient | Ex. 6 | Ex. 7 | Ex. 8 | Ex. 9 | Ex. 10 |
|---|---|---|---|---|---|
| Skim milk | 695.30 kg | 695.30 kg | 695.30 kg | 695.30 kg | 695.30 kg |
| Lactose | 380.80 kg | 380.80 kg | 380.80 kg | 380.80 kg | 380.80 kg |
| High oleic safflower oil | 118.20 kg | 118.20 kg | 118.20 kg | 118.20 kg | 118.20 kg |
| Soy oil | 83.62 kg | 83.62 kg | 83.62 kg | 83.62 kg | 83.62 kg |
| Coconut oil | 82.52 kg | 82.52 kg | 82.52 kg | 82.52 kg | 82.52 kg |
| Galactooligosaccharides | 8 kg | 40 kg | 80 kg | 120 kg | 160 kg |
| Whey protein concentrate | 50.89 kg | 50.89 kg | 50.89 kg | 50.89 kg | 50.89 kg |
| Potassium citrate | 8.93 kg | 8.93 kg | 8.93 kg | 8.93 kg | 8.93 kg |
| Calcium carbonate | 4.38 kg | 4.38 kg | 4.38 kg | 4.38 kg | 4.38 kg |
| ARA oil | 2.86 kg | 2.86 kg | 2.86 kg | 2.86 kg | 2.86 kg |
| Nucleotide-choline premix | 2.40 kg | 2.40 kg | 2.40 kg | 2.40 kg | 2.40 kg |
| Ascorbic acid | 1.28 kg | 1.28 kg | 1.28 kg | 1.28 kg | 1.28 kg |
| Potassium chloride | 1.24 kg | 1.24 kg | 1.24 kg | 1.24 kg | 1.24 kg |
| Soy lecithin | 1.12 kg | 1.12 kg | 1.12 kg | 1.12 kg | 1.12 kg |
| Vitamin/mineral/taurine premix | 1.12 kg | 1.12 kg | 1.12 kg | 1.12 kg | 1.12 kg |
| DHA oil | 1.07 kg | 1.07 g | 1.07 kg | 1.07 kg | 1.07 kg |
| Magnesium chloride | 948.50 g | 948.50 g | 948.50 g | 948.50 g | 948.50 g |
| Vitamin A, D, E, K1 | 518.40 g | 518.40 g | 518.40 g | 518.40 g | 518.40 g |
| Ferrous sulfate | 472.40 g | 472.40 g | 472.40 g | 472.40 g | 472.40 g |
| Choline chloride | 432.10 g | 432.10 g | 432.10 g | 432.10 g | 432.10 g |
| Ascorbyl palmitate | 364.90 g | 364.90 g | 364.90 g | 364.90 g | 364.90 g |
| Sodium chloride | 347.50 g | 347.50 g | 347.50 g | 347.50 g | 347.50 g |
| Carotenoid premix | 187.4 g | 187.4 g | 187.4 g | 187.4 g | 187.4 g |
| Mixed tocopherols | 161.20 g | 161.20 g | 161.20 g | 161.20 g | 161.20 g |
| L-carnitine | 26.30 g | 26.30 g | 26.30 g | 26.30 g | 26.30 g |
| Riboflavin | 3.18 g | 3.18 g | 3.18 g | 3.18 g | 3.18 g |
| Tricalcium phosphate | AN | AN | AN | AN | AN |
| Potassium phosphate monobasic | AN | AN | AN | AN | AN |
| Potassium hydroxide | AN | AN | AN | AN | AN |

AN = as needed

| Ingredient | Ex. 11 | Ex. 12 | Ex. 13 | Ex. 14 | Ex. 15 |
|---|---|---|---|---|---|
| Water | 793.7 kg | 793.7 kg | 793.7 kg | 793.7 kg | 793.7 kg |
| Nonfat milk | 97.50 kg | 97.50 kg | 97.50 kg | 97.50 kg | 97.50 kg |
| Corn syrup solids | 31.90 kg | 31.90 kg | 31.90 kg | 31.90 kg | 31.90 kg |
| Medium chain triglycerides | 17.20 kg | 17.20 kg | 17.20 kg | 17.20 kg | 17.20 kg |
| Lactose | 16.45 kg | 16.45 kg | 16.45 kg | 16.45 kg | 16.45 kg |
| Whey protein concentrate | 12.69 kg | 12.69 kg | 12.69 kg | 12.69 kg | 12.69 kg |
| Galactooligosaccharides | 8 kg | 40 kg | 80 kg | 120 kg | 160 kg |
| Soy oil | 10.30 kg | 10.30 kg | 10.30 kg | 10.30 kg | 10.30 kg |
| Coconut oil | 6.30 kg | 6.30 kg | 6.30 kg | 6.30 kg | 6.30 kg |
| 5% KOH | 4.86 kg | 4.86 kg | 4.86 kg | 4.86 kg | 4.86 kg |
| Tricalcium phosphate | 2.56 kg | 2.56 kg | 2.56 kg | 2.56 kg | 2.56 kg |
| Vitamin/mineral/taurine premix | 1.12 kg | 1.12 kg | 1.12 kg | 1.12 kg | 1.12 kg |
| Magnesium chloride | 405.00 g | 405.00 g | 405.00 g | 405.00 g | 405.00 g |
| Soy lecithin | 364.00 g | 364.00 g | 364.00 g | 364.00 g | 364.00 g |
| Monoglycerides | 364.00 g | 364.00 g | 364.00 g | 364.00 g | 364.00 g |
| AA fungal oil | 364.00 g | 364.00 g | 364.00 g | 364.00 g | 364.00 g |
| Potassium citrate | 340.00 g | 340.00 g | 340.00 g | 340.00 g | 340.00 g |
| Carrageenan | 300.00 g | 300.00 g | 300.00 g | 300.00 g | 300.00 g |
| Nucleotide-choline premix | 293.00 g | 293.00 g | 293.00 g | 293.00 g | 293.00 g |
| Sodium citrate | 250.00 g | 250.00 g | 250.00 g | 250.00 g | 250.00 g |
| DHA oil | 230.00 g | 230.00 g | 230.00 g | 230.00 g | 230.00 g |
| Potassium chloride | 138.00 g | 138.00 g | 138.00 g | 138.00 g | 138.00 g |
| Calcium carbonate | 101.00 g | 101.00 g | 101.00 g | 101.00 g | 101.00 g |
| Magnesium chloride | 948.50 g | 948.50 g | 948.50 g | 948.50 g | 948.50 g |
| Mixed Carotenoid Suspension | 110.23 g | 110.23 g | 110.23 g | 110.23 g | 110.23 g |
| Vitamin A, D3, E, K1 | 82.60 g | 82.60 g | 82.60 g | 82.60 g | 82.60 g |
| Choline chloride | 35.48 g | 35.48 g | 35.48 g | 35.48 g | 35.48 g |
| L-carnitine | 30.7 g | 30.7 g | 30.7 g | 30.7 g | 30.7 g |
| Vitamin A palmitate | 313.00 mg | 313.00 mg | 313.00 mg | 313.00 mg | 313.00 mg |
| Sodium chloride | AN | AN | AN | AN | AN |
| Potassium phosphate | AN | AN | AN | AN | AN |

AN = as needed

Examples 16-19

Examples 16-19 illustrate concentrated liquid human milk fortifiers of the present disclosure, the ingredients of which are listed in the table below. All ingredient amounts are listed as kilogram or pound per 18,000 pounds batch of product, unless otherwise specified.

| Ingredient (Per 18,000 pounds) | Ex. 16 | Ex. 17 | Ex. 18 | Ex. 19 |
|---|---|---|---|---|
| Nonfat milk solids | 7220.00 lbs | 7220.00 lbs | 7220.00 lbs | 7220.00 lbs |
| Corn syrup solids | 2870.00 lbs | 2870.00 lbs | 2870.00 lbs | 2870.00 lbs |
| Medium chain triglycerides | 1760.00 lbs | 1760.00 lbs | 1760.00 lbs | 1760.00 lbs |
| Whey protein concentrate | 3410.00 lbs | 3410.00 lbs | 3410.00 lbs | 3410.00 lbs |
| Tricalcium phosphate | 701.00 kg | 701.00 kg | 701.00 kg | 701.00 kg |
| Galactooligosaccharides | 164 kg | 350 kg | 650 kg | 818 kg |
| Potassium citrate tribasic | 224.00 kg | 224.00 kg | 224.00 kg | 224.00 kg |
| Ascorbic acid | 136.00 kg | 136.00 kg | 136.00 kg | 136.00 kg |
| Magnesium chloride | 117.00 kg | 117.00 kg | 117.00 kg | 117.00 kg |
| Sodium chloride | 4.71 kg | 4.71 kg | 4.71 kg | 4.71 kg |
| m-Inositol | 11.00 kg | 11.00 kg | 11.00 kg | 11.00 kg |
| Sodium citrate tribasic | 23.90 kg | 23.90 kg | 23.90 kg | 23.90 kg |
| Ferrous sulfate | 4.00 kg | 4.00 kg | 4.00 kg | 4.00 kg |
| Soy lecithin | 16.80 kg | 16.80 kg | 16.80 kg | 16.80 kg |
| Zinc sulfate | 11.1 kg | 11.1 kg | 11.1 kg | 11.1 kg |
| Vitamin E acetate | 7.60 kg | 7.60 kg | 7.60 kg | 7.60 kg |
| Vitamin A palmitate | 2.40 kg | 2.40 kg | 2.40 kg | 2.40 kg |
| Niacinamide | 9.80 kg | 9.80 kg | 9.80 kg | 9.80 kg |
| Riboflavin | 1.1 kg | 1.1 kg | 1.1 kg | 1.1 kg |
| Calcium pantothenate | 4.40 kg | 4.40 kg | 4.40 kg | 4.40 kg |
| Cupric sulfate | 1.800 kg | 1.800 kg | 1.800 kg | 1.800 kg |
| Thiamine hydrochloride | 776.00 g | 776.00 g | 776.00 g | 776.00 g |
| Pyridoxine hydrochloride | 665.00 g | 665.00 g | 665.00 g | 665.00 g |
| Vitamin D3 | 359.00 g | 359.00 g | 359.00 g | 359.00 g |
| Biotin | 82.00 g | 82.00 g | 82.00 g | 82.00 g |
| Folic acid | 77.00 g | 77.00 g | 77.00 g | 77.00 g |
| Cyanocobalamin | 2.00 g | 2.00 g | 2.00 g | 2.00 g |
| Phylloquinone | 27.00 g | 27.00 g | 27.00 g | 27.00 g |
| Manganese sulfate | 51.00 g | 51.00 g | 51.00 g | 51.00 g |
| Sodium selenate | 1.10 g | 1.10 g | 1.10 g | 1.10 g |

-continued

| Ingredient (Per 18,000 pounds) | Ex. 16 | Ex. 17 | Ex. 18 | Ex. 19 |
| --- | --- | --- | --- | --- |
| Calcium carbonate | 0-4 kg | 0-4 kg | 0-4 kg | 0-4 kg |
| Potassium phosphate monobasic | 0-32 kg | 0-32 kg | 0-32 kg | 0-32 kg |
| Potassium hydroxide | 24.00 kg | 24.00 kg | 24.00 kg | 24.00 kg |

Example 20

In this Example, the effect of GOS on increasing the expression of TFF3 and other goblet cells that promote gastrointestinal healing is analyzed.

GOS is tested with respect to its ability to induce MUC-2, TFF3, RELMb, CHST5, and GAL3ST2 expression in the human LS174T cell culture model of goblet cells. The human LS174T colorectal cancer cell line is obtained from the American Type Culture Collection (ATCC). LS174T cells are maintained in minimum essential medium (MEM) supplemented with 10% Fetalplex (Gemini Biosciences), 1.5 g/L of $Na_2CO_3$, 10 ml/L penicillin G-streptomycin solution (Gemini Bio-products) at 37° C. in 5% $CO_2$. GOS (Purimine GO-P90) is obtained from GTC Nutrition (Westchester, Ill.) and dissolved in cell culture grade water to required concentration. The solution is subsequently filter sterilized and used for cell culture studies. The endotoxin level of GOS solution is measured by LAL assay kit (Gen Script) and found to be less than 0.5 EU/ml (Endotoxin Units/ml). LS174T cells are treated with the media described above but with or without 8 g GOS/L for 72 hours.

LS174T cells are collected and suspended in Trizol reagent and total RNA is isolated using the RNeasy Plus Kit (Qiagen) according to the manufacturer's instructions. The quality and quantity of RNA isolates are determined by Nanodrop (Thermo Fisher Scientific). RNA isolates are reverse transcribed using the High Capacity cDNA Reverse Transcription Kit (Applied Biosystems) to create cDNA, which is to assess gene expression via quantitative PCR.

For quantitative RT-PCR, specific TaqMAN gene expression assays are obtained from Applied Biosystems, which include expression assays for MUC-2 (Hs00159374_m1), TFF3 (Hs00173625_m1), RELMB (Hs00395669_m1), CHST5 (Hs00375495_m1), GAL3ST2 (Hs00223271_m1) and GUSB (Hs99999908_m1). Quantitative real-time PCR is performed using TaqMAN PCR Master Mix (Applied Biosystems). Reactions are run in duplicates in a 384-well plate using an Applied Biosystems 7900HT Fast Real-Time PCR System. The results are analyzed using SDS 2.3 software and calculated by delta delta Ct method. All samples are normalized to Gus-β expression and fold induction is calculated over untreated controls. Gene expression is expressed as fold increase compared to GOS-free control cells. The experiment is repeated three times. Data represent means+SEM (n=3 plates per experiment). Statistical differences are indicated by different letters ($P<0.05$).

Figure 1B:
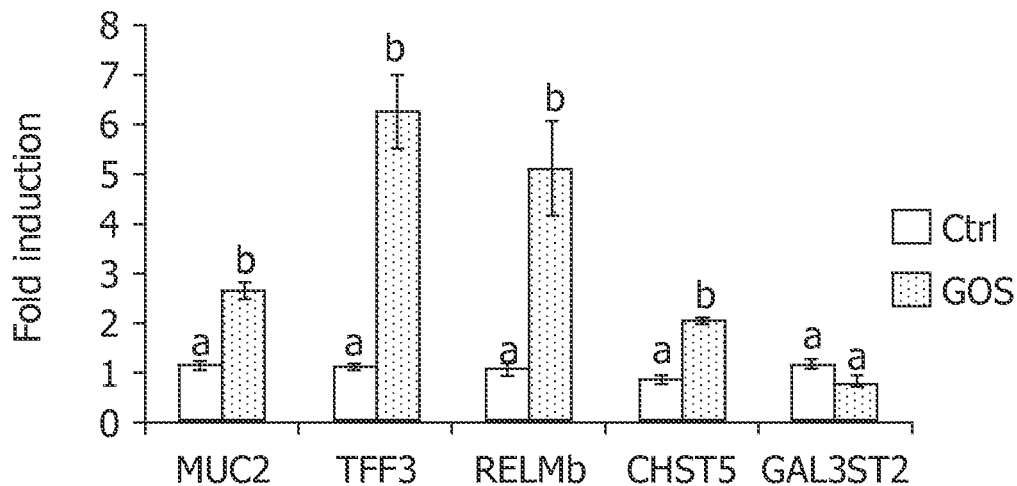
Figure 1C:
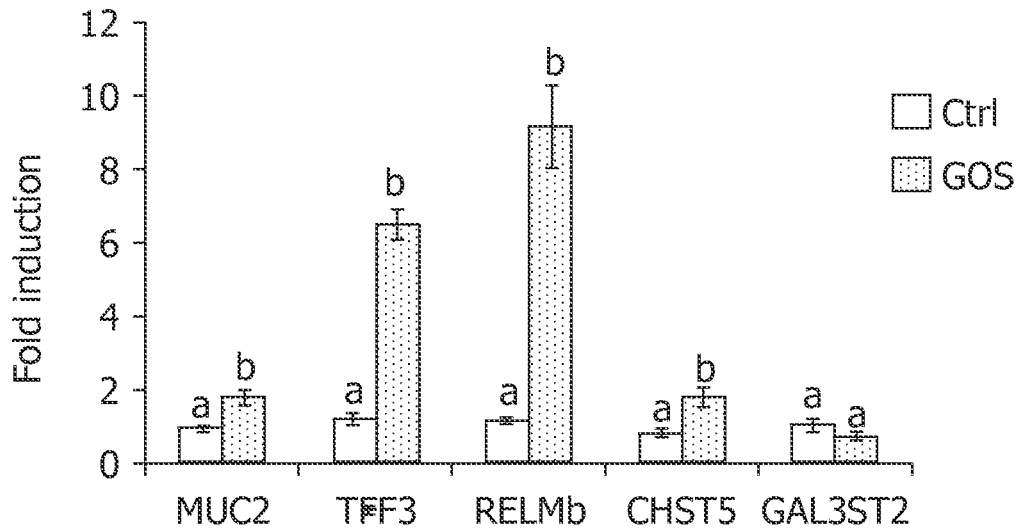
Figure 2A:
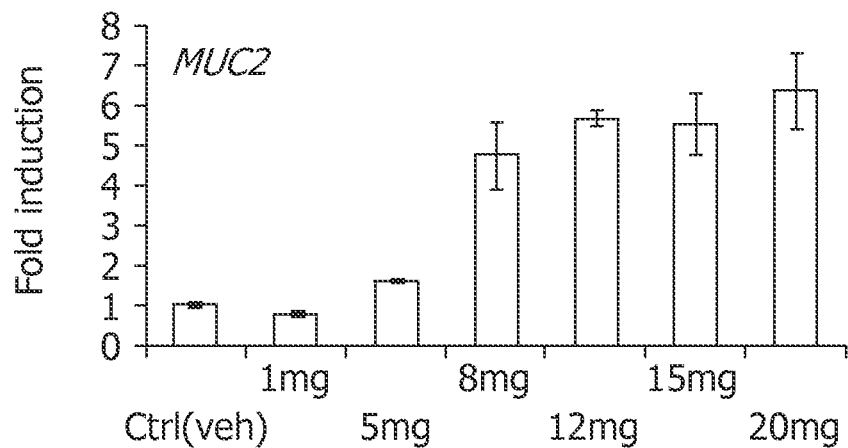
FIGS. 2A-2E are charts depicting the dose dependency of galactooligosaccharides on the expression of several genes involved in the healing response of the gastrointestinal tract as measured in Example 21.
Figure 2B:
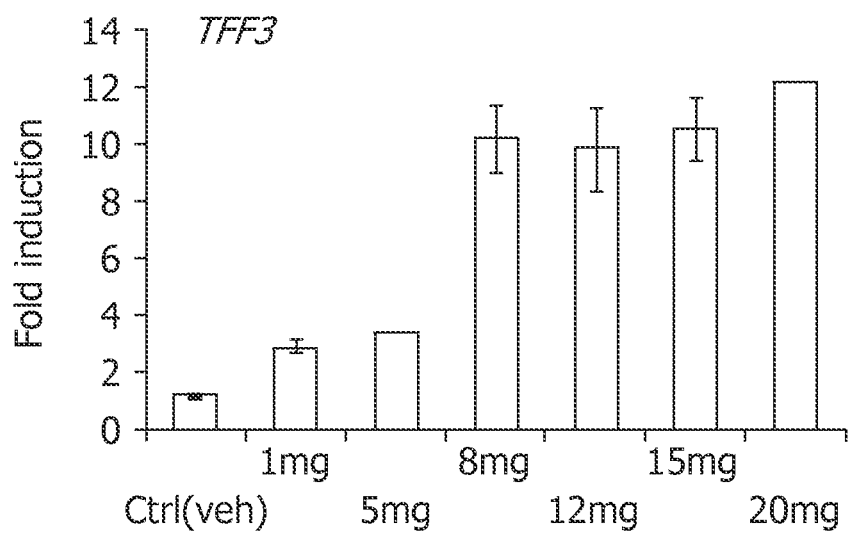
Figure 2C:
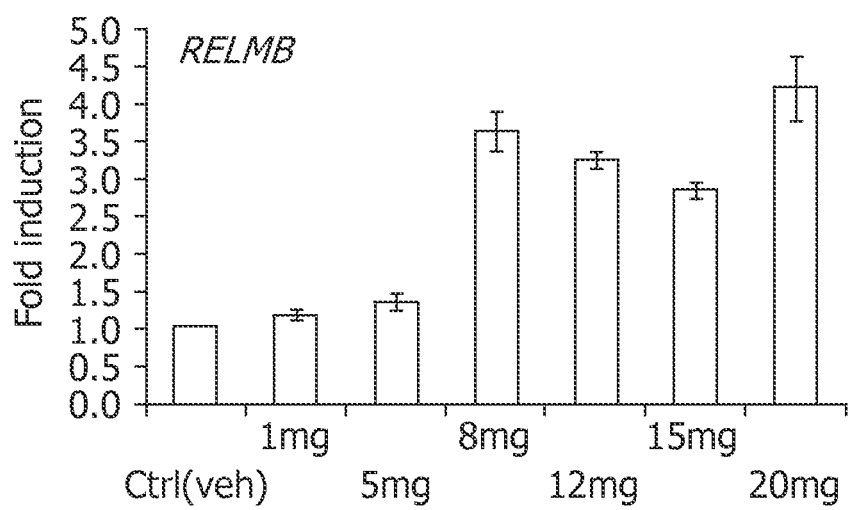
Figure 2D:
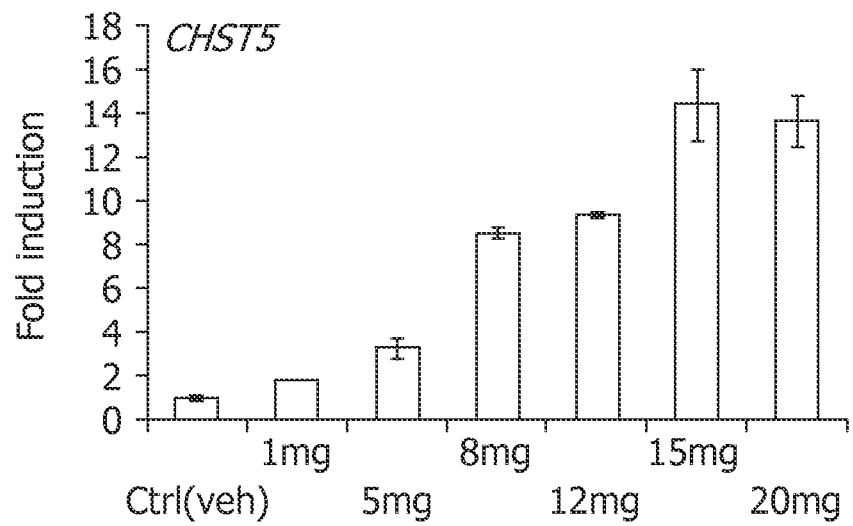
Figure 2E:
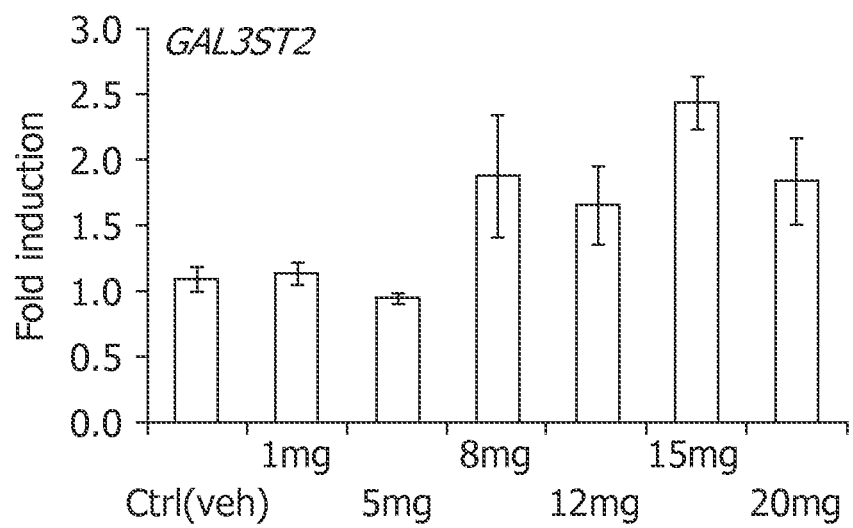

FIGS. 1A-1C represent the results of three replicate experiments. In each experiment, the treatment with GOS at a level of 8 g/L consistently and significantly increases the expression of the TFF3 gene 6-7 fold compared to control cultures. Additionally, expression of the genes encoding MUC-2, RELMb, and CHST5 are consistently and significantly increased by 2-3, 5-9, and 2-3 fold, respectively. Increased expression of goblet cell genes is specific and not universal, as evidenced by the lack of induction of GAL3ST2 by treatment with GOS at 8 g/L.

These results indicate that GOS promotes the expression of several genes involved in the healing response of the GI tract. First, expression of TFF3, which GOS is shown to enhance, has been positively associated with prevention and restitution of gastrointestinal damage to the epithelial cells in the intestine of mammals. Oral treatment with TFF3 reduces the damage associated with different forms of colitis in animal models. Additionally, GOS induced the expression of MUC-2, which provides a barrier that protects the gastrointestinal tract from infection and other sources of injury. Further, GOS induced the expression of RELMb, which is a protein associated with resolution of inflammation. Because tissue damage is difficult to heal when inflammation is abundant, the inflammation resolving effects of RELMb induced by GOS also supports healing. The combined impact of GOS on expression of TFF3, MUC-2 and RELMb enables a product to support wound healing through its synergistic effects on cell healing, resolution of inflammation, and promotion of barrier function.

Example 21

In this Example, the dose-dependency of the induction of expression of TFF3 and other goblet cells that promote gastrointestinal healing by GOS is analyzed.

GOS is tested with respect to its ability to dose-dependently induce MUC-2, TFF3, RELMb, CHST5, and GAL3ST2 expression in the human LS174T cell culture model of goblet cells. The human LS174T colorectal cancer cell line is obtained from the American Type Culture Collection (ATCC). LS174T cells are maintained in minimum essential medium (MEM) supplemented with 10% Fetalplex (Gemini Biosciences), 1.5 g/L of $Na_2CO_3$, 10 ml/L penicillin G-streptomycin solution (Gemini Bio-products) at 37° C. in 5% $CO_2$. GOS (Purimine GO-P90) is obtained from GTC Nutrition (Westchester, Ill.) and dissolved in cell culture grade water to required concentration. The solution is subsequently filter sterilized and used for cell culture studies. The endotoxin level of GOS solution is measured by LAL assay kit (Gen Script) and found to be less than 0.5 EU/ml (Endotoxin Units/ml). LS174T cells are treated with the media described above containing 0, 1, 5, 8, 12, 15, or 20 g GOS/L.

LS 174T cells are collected and suspended in Trizol reagent and total RNA is isolated using the RNeasy Plus Kit (Qiagen) according to the manufacturer's instructions. The quality and quantity of RNA isolates are determined by Nanodrop (Thermo Fisher Scientific). RNA isolates are reverse transcribed using the High Capacity cDNA Reverse Transcription Kit (Applied Biosystems) to create cDNA, which is to assess gene expression via quantitative PCR.

For quantitative RT-PCR, specific TaqMAN gene expression assays are obtained from Applied Biosystems, which includes expression assays for MUC-2 (Hs00159374_m1), TFF3 (Hs00173625_m1), RELMB (Hs00395669_m1), CHST5 (Hs00375495_m1), GAL3ST2 (Hs00223271_m1) and GUSB (Hs99999908_m1). Quantitative real-time PCR is performed using TaqMAN PCR Master Mix (Applied Biosystems). Reactions are run in duplicates in a 384-well plate using an Applied Biosystems 7900HT Fast Real-Time PCR System. The results are analyzed using SDS 2.3 software and calculated by delta delta Ct method. All samples are normalized to Gus-β expression and fold induction is calculated over untreated controls. Gene expression is expressed as fold increase compared to GOS-free control cells. The experiment is repeated three times. Data represent means+SEM (n=3 plates per experiment). Statistical differences are indicated by different letters (P<0.05).

FIGS. 2A-2E represent the combined results of three replicate experiments. Specifically, FIG. 2B indicates a dose dependent increase in expression of TFF3, with a modest induction (~3 fold) noted at the 1 mg/mL and 5 mg/mL treatment levels and more pronounced increases (10-12 fold) at 8 mg/mL and higher. Similarly the expression levels of MUC-2 (FIG. 2A), RELMb (FIG. 2C), and CHST5 (FIG. 2D) are only modestly or not affected at GOS levels of 1-5 mg/mL but are markedly elevated (5-6 fold for MUC-2, 3-4 fold for RELMb, and 8-14 fold for CHST5) in response to treatment with GOS at levels of 8 mg/mL or higher. In contrast, gene expression of GAL3ST2 (FIG. 2E) is not significantly impacted at any dose. As such, it can be concluded that the impact of GOS on expression of several genes involved in the healing response of the gastrointestinal tract is dose-dependent.

Example 22

In this Example, the ability of GOS to promote the ability of probiotics to induce expression of TFF3 and other goblet cells that promote gastrointestinal healing is analyzed.

GOS is tested with respect to its impact on the ability of probiotics to induce MUC-2, TFF3, RELMb, CHST5, and GAL3ST2 expression in the human LS174T cell culture model of goblet cells. The human LS174T colorectal cancer cell line is obtained from the American Type Culture Collection (ATCC). LS174T cells are maintained in minimum essential medium (MEM) supplemented with 10% Fetalplex (Gemini Biosciences), 1.5 g/L of $Na_2CO_3$, 10 ml/L penicillin G-streptomycin solution (Gemini Bio-products) at 37° C. in 5% $CO_2$. GOS (Purimine GO-P90) is obtained from GTC Nutrition (Westchester, Ill.) and dissolved in cell culture grade water to required concentration. The solution is subsequently filter sterilized and used for cell culture studies. The endotoxin level of GOS solution is measured by LAL assay kit (Gen Script) and found to be less than 0.5 EU/ml (Endotoxin Units/ml).

Probiotic *Bifidobacterium lactis* cultures are grown in sMRS supplemented with 0.5 g/L cysteine in the presence of 1% glucose or 1% GOS. Culture O.D. is measured at 600 nm and, at stationary phase, the culture supernatant is collected after centrifugation at 4000 rpm for 5 min. The culture supernatant is subsequently filter sterilized and lyophilized. The lyophilized product is herein named the "postbiotic" fraction. Bacterial culture media containing 1% GOS or 1% glucose but not inoculated with *Bifidobacterium lactis* is filtered, lyophilized, and used as the controls for the postbiotic fractions. Postbiotic fractions and control fractions are then added to MEM to represent "postbiotic" and control media, respectively. LS174T cells are treated with postbiotic and control media for 72 hours.

At the end of the incubation period, the LS174T cells are collected and suspended in Trizol reagent. Total RNA is isolated using the RNeasy Plus Kit (Qiagen) according to the manufacturer's instructions. The quality and quantity of RNA isolates are determined by Nanodrop (Thermo Fisher Scientific). RNA isolates are reverse transcribed using the High Capacity cDNA Reverse Transcription Kit (Applied Biosystems) to create cDNA, which is to assess gene expression via quantitative Real-time PCR. Specific TaqMAN gene expression assays are obtained from Applied Biosystems, which includes expression assays for MUC-2 (Hs00159374_m1), TFF3 (Hs00173625_m1), RELMB (Hs00395669_m1), CHST5 (Hs00375495_m1), GAL3ST2 (Hs00223271_m1) and GUSB (Hs99999908_m1). Quantitative real-time PCR is performed using TaqMAN PCR Master Mix (Applied Biosystems). Reactions are run in duplicates in a 384-well plate using an Applied Biosystems 7900HT Fast Real-Time PCR System. The results are analyzed using SDS 2.3 software and calculated by delta delta Ct method. All samples are normalized to Gus-β expression and fold induction is calculated over untreated controls. Gene expression is expressed as fold increase compared to GOS-free control cells. The experiment is repeated three times. Data represent means+SEM (n=2-3 plates per experiment). Statistical differences are indicated by different letters (P<0.05).

Figure 3A:
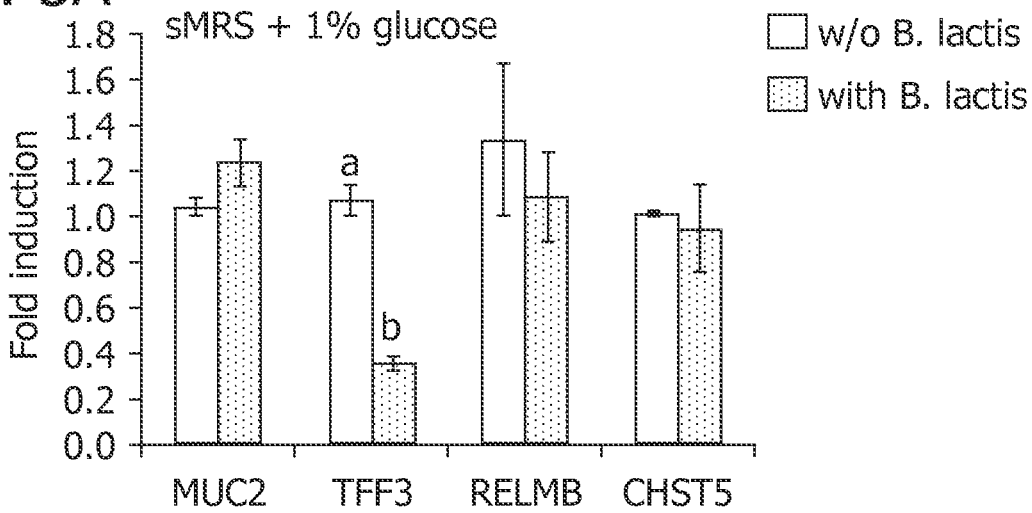
FIGS. 3A and 3B are charts depicting the effect of the combination of galactooligosaccharides and *Bifidobacterium lactis* on the expression of several genes involved in the healing response of the gastrointestinal tract as measured in Example 22.
Figure 3B:
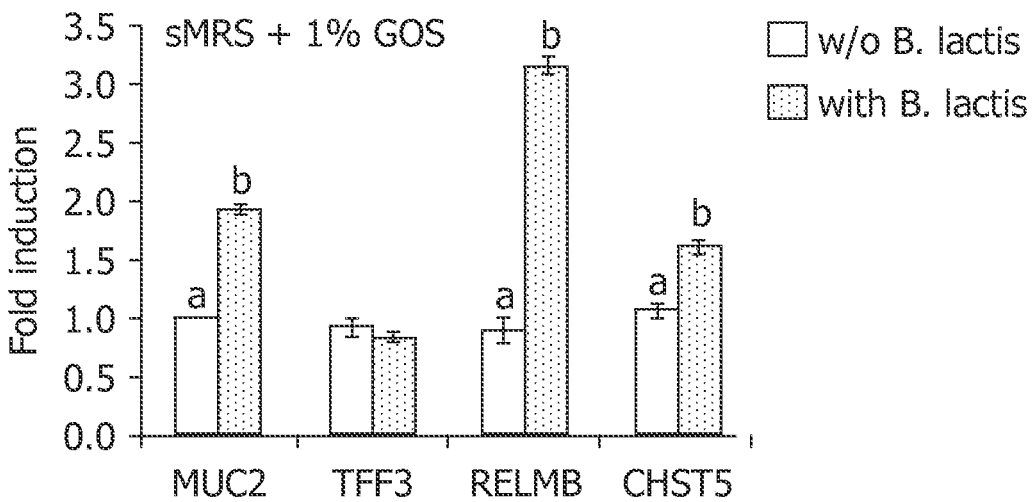
Figure 4A:
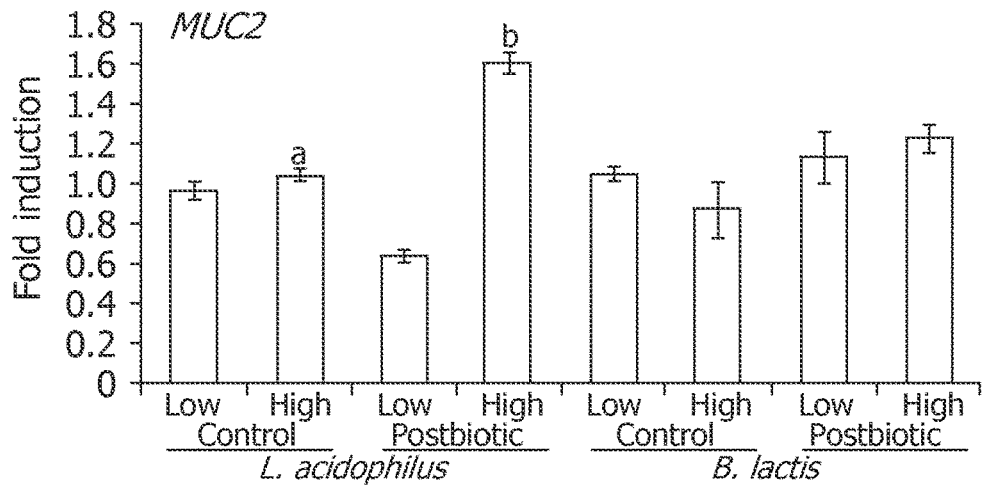
FIGS. 4A-4E are charts depicting the effect of the combinations of galactooligosaccharides and *Bifidobacterium lactis* and galactooligosaccharides and *Lactobacillus acidophilus* on the expression of several genes involved in the healing response of the gastrointestinal tract as measured in Example 23.
Figure 4B:
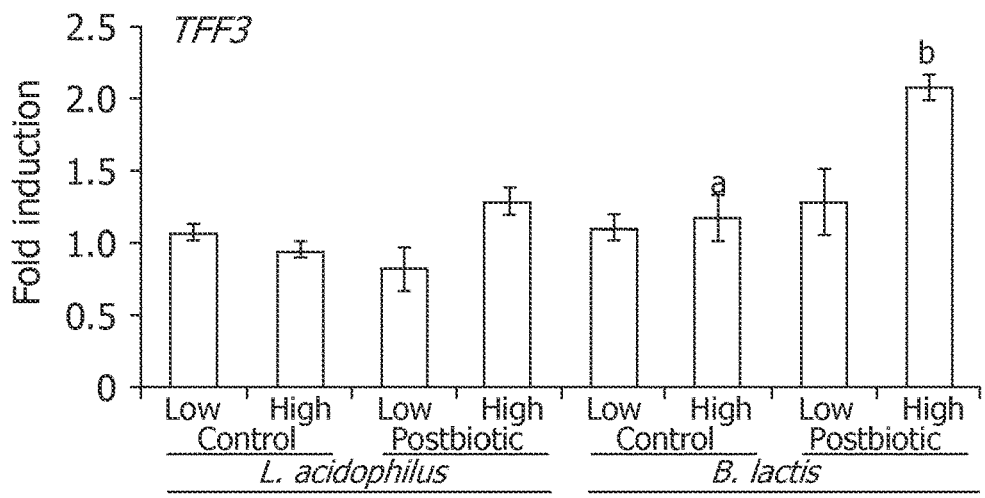
Figure 4C:
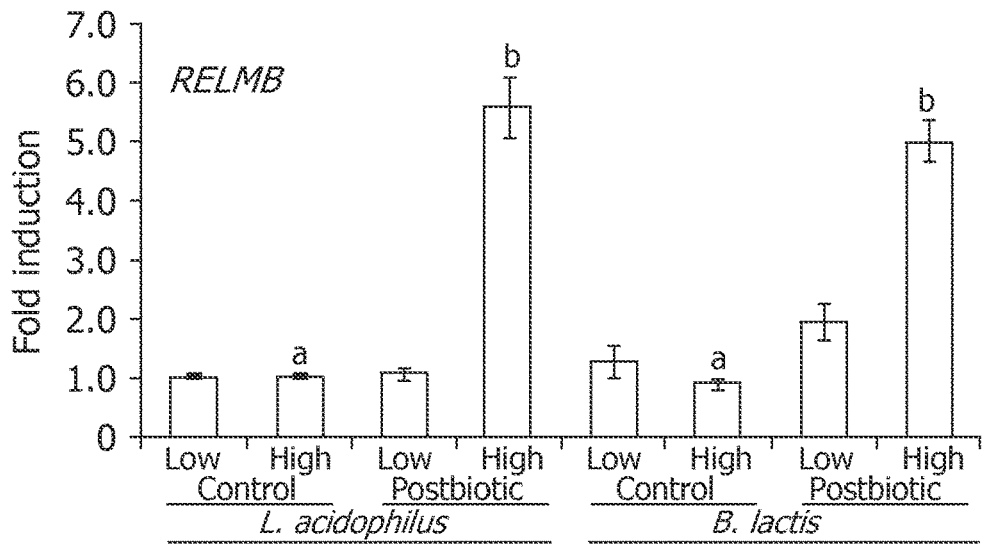
Figure 4D:
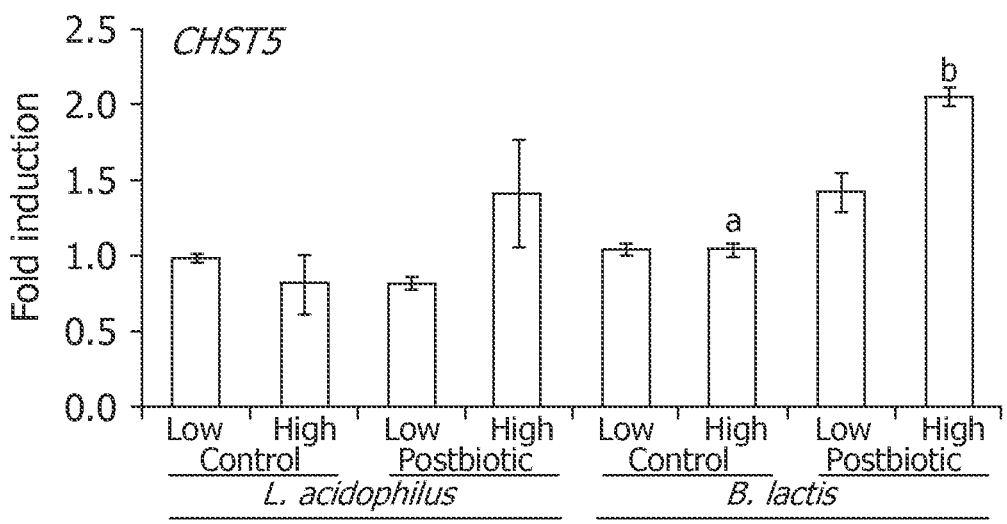
Figure 4E:
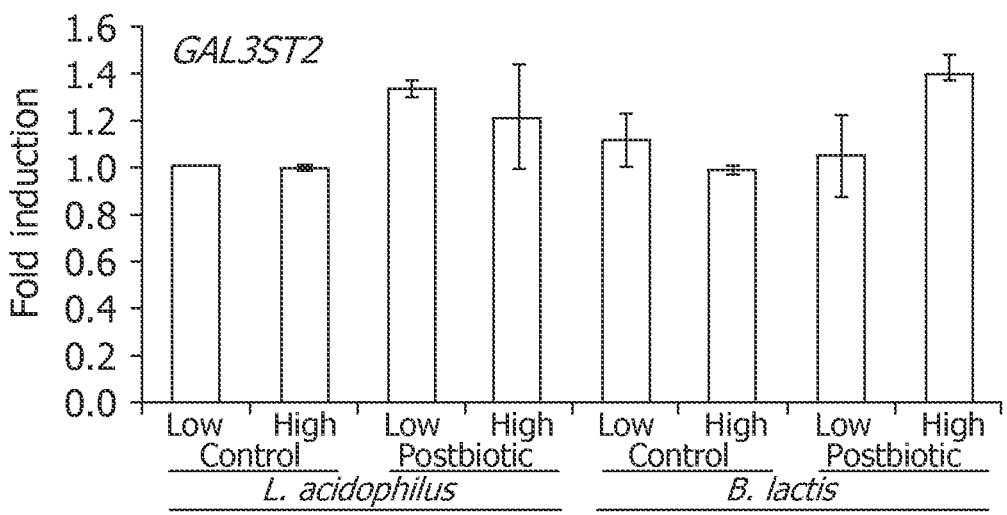

FIG. 3A illustrates the impact of treatment with the *Bifidobacterium lactis*+glucose postbiotic fraction vs. control fraction on the expression of goblet cell products that promote gastrointestinal healing in LS174T cell cultures. The *Bifidobacterium lactis*+glucose postbiotic fraction does not affect the expression levels of MUC-2, RELMb or CHST5. TFF3 expression, however, is reduced by ⅔ by this postbiotic fraction. FIG. 3B illustrates the impact of treatment with the *Bifidobacterium lactis*+GOS postbiotic fraction on the expression of goblet cell products that promote gastrointestinal healing in LS174T cell cultures. This postbiotic fraction significantly increases the expression of MUC-2 (2 fold), RELMb (3 fold), CHST5 (1.5 fold) and does not decrease the expression of TFF3.

These results indicate that incubation of probiotic *Bifidobacterium lactis* with GOS results in production of a supernatant "postbiotic" that induces the expression of genes that can promote gastrointestinal healing. This postbiotic fraction is a model of the products that a probiotic such as *Bifidobacterium lactis* would produce when exposed to GOS in the lumen of an infant's gastrointestinal tract. Therefore these data indicate that infants fed infant formulas including GOS in combination with a *Bifidobacterium lactis* are provided with greater gastrointestinal protection than those given formulas with GOS or *Bifidobacterium lactis* alone.

Example 23

In this Example, the ability of GOS to promote the ability of probiotics to induce expression of TFF3 and other goblet cells is analyzed.

GOS is tested with respect to its impact on the ability of probiotics to induce MUC-2, TFF3, RELMb, CHST5, and GAL3ST2 expression in the human LS174T cell culture model of goblet cells. The human LS174T colorectal cancer cell line is obtained from the American Type Culture Collection (ATCC). LS174T cells are maintained in minimum essential medium (MEM) supplemented with 10% Fetalplex (Gemini Biosciences), 1.5 g/L of $Na_2CO_3$, 10 ml/L penicillin G-streptomycin solution (Gemini Bio-products) at 37° C. in 5% $CO_2$. GOS (Purimine GO-P90) is obtained from GTC Nutrition (Westchester, Ill.) and dissolved in cell culture grade water to required concentration. The solution is subsequently filter sterilized and used for cell culture studies.

The endotoxin level of GOS solution is measured by LAL assay kit (Gen Script) and found to be less than 0.5 EU/ml (Endotoxin Units/ml).

Probiotic *Bifidobacterium lactis* cultures are grown in sMRS supplemented with 0.5 g/L cysteine in the presence of 1% glucose or 1% GOS while probiotic *Lactobacillus acidophilus* cultures are grown in sMRS in the presence of 1% glucose or 1% GOS. Culture O.D. is measured at 600 nm and at stationary phase the culture supernatant is collected after centrifugation at 4000 rpm for 5 min. The culture supernatants are subsequently filter sterilized and lyophilized. The lyophilized products are herein named the "postbiotic" fraction. Bacterial culture media containing 1% GOS or 1% glucose but not inoculated with probiotic is filtered, lyophilized, and used as the controls for the postbiotic fractions. Postbiotic fractions and control fractions are then added to MEM to represent "postbiotic" and control media, respectively. LS174T cells are treated with postbiotic and control media for 72 hours.

At the end of the incubation period, the LS174T cells are collected and suspended in Trizol reagent. Total RNA is isolated using the RNeasy Plus Kit (Qiagen) according to the manufacturer's instructions. The quality and quantity of RNA isolates are determined by Nanodrop (Thermo Fisher Scientific). RNA isolates are reverse transcribed using the High Capacity cDNA Reverse Transcription Kit (Applied Biosystems) to create cDNA, which is to assess gene expression via quantitative Real-time PCR. Specific TaqMAN gene expression assays are obtained from Applied Biosystems, which include expression assays for MUC-2 (Hs00159374_m1), TFF3 (Hs00173625_m1), RELMB (Hs00395669_m1), CHST5 (Hs00375495_m1), GAL3ST2 (Hs00223271_m1) and GUSB (Hs99999908_m1). Quantitative real-time PCR is performed using TaqMAN PCR Master Mix (Applied Biosystems). Reactions are run in duplicates in a 384-well plate using an Applied Biosystems 7900HT Fast Real-Time PCR System. The results are analyzed using SDS 2.3 software and calculated by delta delta Ct method. All samples are normalized to Gus-β expression and fold induction is calculated over untreated controls. Gene expression is expressed as fold increase compared to GOS-free control cells. Data represent means+SEM (n=3). Statistical differences are indicated by different letters ($P<0.05$).

FIGS. 4A-4E report the impact of treatment with the *B. lactis* postbiotic fraction or *L. acidophilus* postbiotic fraction vs. control fractions on the expression of goblet cell products that promote gastrointestinal healing in LS174T cell cultures. Treatment of those cells with *L. acidophilus* postbiotic fraction significantly increases the expression of MUC-2 and RELMb but only at the high dose. The *L. acidophilus* postbiotic does not impact the expression of TFF3, CHST5 or GAL3ST2. Treatment of LS174T cells with *B. lactis* postbiotic fraction significantly increases TFF3, RELMb and CHST5 expression but only at the highest dose. MUC-2 and GAL3ST2 expression are not significantly increased by treatment with that postbiotic fraction.

These results indicate that incubation of probiotic *B. lactis* or *L. acidophilus* with GOS results in production of a supernatant "postbiotic" that induces the expression of genes that can promote gastrointestinal healing. This postbiotic fraction is a model of the products that a probiotic, such as *B. lactis* or *L. acidophilus*, would produce when exposed to GOS in the lumen of an infant's gastrointestinal tract. Therefore, these data indicate that infants fed formulas including GOS and *B. lactis* or GOS and *L. acidophilus* are provided with greater gastrointestinal protection than those given formulas with *B. lactis*, *L. acidophilus* or GOS alone.

What is claimed is:

1. A method of stimulating a healing response of the gastrointestinal tract of an individual, the method comprising:
   identifying an individual having an injured gastrointestinal tract; and
   administering to the individual a nutritional composition comprising a galacto-oligosaccharide in a concentration of from 8 kg/1000 kg of the nutritional composition to 160 kg/1000 kg of the nutritional composition; wherein the gastrointestinal tract is injured as a result of at least one of antibiotic therapy, radiation therapy, chemotherapy, surgery, enteric infection, inflammatory bowel disease, colitis, and chronic stress.

2. The method of claim 1, wherein the nutritional composition is selected from the group consisting of a human milk fortifier, an infant formula, a pediatric formula, a follow on formula, and an adult nutritional composition.

3. The method of claim 1, wherein the nutritional composition further comprises at least one human milk oligosaccharide.

4. The method of claim 1, wherein the nutritional composition further comprises at least one probiotic.

5. The method of claim 4, wherein the probiotic is selected from the group consisting of *Bifidobacterium lactis*, *Lactobacillus acidophilus*, and combinations thereof.

6. The method of claim 1, wherein the nutritional composition comprises
   protein in an amount of about 7.5% to about 25% of the caloric content;
   carbohydrate in an amount of about 35% to about 50% of the total caloric content; and
   fat component in an amount of about 35% to about 60% of the total caloric content.

7. A method of stimulating a healing response of the gastrointestinal tract of an individual, the method comprising:
   identifying an individual having an injured gastrointestinal tract; and administering to the individual a nutritional composition comprising protein, fat, carbohydrate, and a galacto-oligosaccharide in a concentration of from 8 g/L of the nutritional composition to 160 g/L of the nutritional composition; wherein the healing response comprises increased expression of at least one mucin-associated protein and the mucin-associated protein is selected from the group consisting of TFF3, MUC-2, and RELMb.

8. The method of claim 7, wherein the nutritional composition comprises
   protein in an amount of about 7.5% to about 25% of the caloric content;
   carbohydrate in an amount of about 35% to about 50% of the total caloric content; and
   fat component in an amount of about 35% to about 60% of the total caloric content.

* * * * *